US011129337B2

(12) United States Patent
Notaguchi

(10) Patent No.: US 11,129,337 B2
(45) Date of Patent: Sep. 28, 2021

(54) GRAFTED PLANT BODY AND METHOD FOR PRODUCING SAME

(71) Applicant: National University Corporation Nagoya University, Aichi (JP)

(72) Inventor: Michitaka Notaguchi, Aichi (JP)

(73) Assignee: National University Corporation Nagoya University, Aichi (JP)

( * ) Notice: Subject to any disclaimer, the term of this patent is extended or adjusted under 35 U.S.C. 154(b) by 0 days.

(21) Appl. No.: 15/509,125

(22) PCT Filed: Oct. 15, 2015

(86) PCT No.: PCT/JP2015/079118
§ 371 (c)(1),
(2) Date: Mar. 6, 2017

(87) PCT Pub. No.: WO2016/060189
PCT Pub. Date: Apr. 21, 2016

(65) Prior Publication Data
US 2017/0347531 A1  Dec. 7, 2017

(30) Foreign Application Priority Data
Oct. 17, 2014  (JP) .............................. JP2014-212889

(51) Int. Cl.
| | |
|---|---|
| *A01G 2/30* | (2018.01) |
| *A01H 5/00* | (2018.01) |
| *G01N 33/46* | (2006.01) |
| *A01H 6/78* | (2018.01) |
| *A01H 6/88* | (2018.01) |
| *A01H 6/74* | (2018.01) |
| *A01H 5/08* | (2018.01) |
| *A01H 5/10* | (2018.01) |
| *A01H 5/12* | (2018.01) |
| *G01N 33/00* | (2006.01) |

(52) U.S. Cl.
CPC ............... *A01G 2/30* (2018.02); *A01H 5/00* (2013.01); *A01H 5/08* (2013.01); *A01H 5/10* (2013.01); *A01H 5/12* (2013.01); *A01H 6/7409* (2018.05); *A01H 6/749* (2018.05); *A01H 6/7418* (2018.05); *A01H 6/78* (2018.05); *A01H 6/88* (2018.05); *G01N 33/0098* (2013.01); *G01N 33/46* (2013.01)

(58) Field of Classification Search
CPC ..................................................... A01G 2/30
See application file for complete search history.

(56) References Cited

U.S. PATENT DOCUMENTS

2017/0347531 A1   12/2017   Notaguchi
2019/0029185 A1   1/2019    Notaguchi

FOREIGN PATENT DOCUMENTS

| | | |
|---|---|---|
| CN | 101743820 | 6/2010 |
| JP | H02-042920 A | 2/1990 |
| JP | H06-253680 A | 9/1994 |
| JP | H07-143820 A | 6/1995 |
| JP | 2007-135572 A | 6/2007 |
| JP | WO2016/060189 A1 | 4/2016 |

OTHER PUBLICATIONS

Rubiales et al 2011, Parasitic Plants, In: Encyclopedia of Life Sciences, John Wiley & Sons, Ltd: Chichester, 10 pages.*
Flaishman et al 2008, Journal of Plant Growth Regulation 27: 231-239.*
Turnbull 2010, Chapter 2, Plant Developmental Biology, Methods in Molecular Biology 655: 11-25.*
Notaguchi et al 2012, Jounal of Integrative Plant Biology, Supporting InformationKaddoura et al 1991, Annals of Botany 68: 547-556.*
Notaguchi et al 2012, Jounal of Integrative Plant Biology, Supporting Information.*
Notaguchi et al 2012, Journal of Integrative Plant Biology 54(10): 760-772.*
Notaguchi et al 2012, Journal of Integrative Plant Biology 54(10), Supporting Information.*
Zeevart Mededelingen van de Landbouwhogeschool te Wageningen/Nederland Flower Formation as Studied by Grafting vol. 58 No. 3 pp. 1-88 (Year: 1956).*
Schroter, Hans-Botho Archive der Pharmazie und Berichte der Deutschen Pharmzeutischen Gesellschaft vol. 288/60, No. 3, pp. 141-145 published in German (Year: 1955).*
Schroter, Hans-Botho Archive der Pharmazie und Berichte der Deutschen Pharmzeutischen Gesellschaft vol. 288/60, No. 3, pp. 141-145 USPTO English Translation dated Jul. 10, 2019 (Year: 1955).*
Mudge et al Horticultural Reviews vol. 35, Chapter 9, pp. 437-493 (Year: 2009).*
Goldschmidt, E.E. Frontiers in Plant Science vol. 5, Article 727, 9 pages (Year: 2014).*
Nickell, "Heteroplastic Grafts", Science, Oct. 8, 1948, vol. 108, p. 389.
Notaguchi et al: "Graft-transmissible action of *Arabidopsis* Flowering Locus T protein to promote flowering," Plant Signaling & Behavior, vol. 4, No. 2, pp. 123-125, Feb. 28, 2009.
Extended Search Report issued to European counterpart application No. 15850625.3.
Flaishman, et al. "*Arabidopsis thaliana* as a Model System for Graft Union Development in Homografts and Heterografts", Journal of Plant Grown Regulation, 2008, vol. 27, p. 231-239.
Zeevart, J.A.D., "Flower Formation as Studied by Grafting", 1958, vol. 58, No. 3, p. 1-88.
First Examination Report dated Aug. 16, 2018 for Australian patent application No. 2015331371.
Zhang et al "Advanced Vegetable Physiology" Edition 1, pp. 22-23, 2008.

(Continued)

*Primary Examiner* — David H Kruse
(74) *Attorney, Agent, or Firm* — Cesari & McKenna, LLP

(57) ABSTRACT

Provided is a novel plant body comprising a plant tissue of a plant belonging to the family Solanaceae, Brassicaceae, Lamiaceae, or Orobanchaceae, wherein graft incompatibility is avoided or suppressed by using a graft medium between different-family plants.

15 Claims, 13 Drawing Sheets

(56) References Cited

OTHER PUBLICATIONS

Han et al "Concise Technology for Vegetable Grafting" Edition 1, pp. 24-26, 2004.
Office Action dated Jun. 27, 2019 for Chinese Patent Application No. 201580048545.2.
Office Action dated Dec. 10, 2019 for Japanese Patent Application No. 2017-184449.
Lunyan; Botany, Higher Education Press, (Issued on Aug. 31, 1961, Revised in 1965), vol. 1, p. 231 Section 2, Artificial Nutrition Reproduction.
Baozhang et al; Plant Physiology; Theoretical Tutorial, China Agricultural Science and Technology Press, Dec. 31, 1996, vol. 1, p. 190.
Bonian et al; Horticultural Plant Propagation, Shanghai Science and Technology Press, Jul. 31,1994, pp. 238-239.
Guoshu; Preliminary Report on Selection of Dwarfing Intermediate Stocks of Pyrus; Nov. 1, 1991, Abstract, pp. 13-15.
Office Action dated Mar. 10, 2020 for Chinese Patent Application No. 201580048545.2.
Hartmann "Theoretical Aspects of Grafting and Budding" Asexual Propagation Chapter 11, pp. 314-427, 1975.
Lei "Grafting Adapter" Science vol. 369, pp. 698-702, 2020.
McCann "Chimeric Plants—The Best of Both Worlds" Science vol. 369, pp. 618-619, 2020.
Notaguchi et al "Cell-Cell Adhesion in Plant Grafting is Facilitated by β-1,4-Glucanases" Science vol. 369, pp. 698-702, 2020.
Notaguchi et al "Cell-Cell Adhesion in Plant Grafting is Facilitated by β-1,4-Glucanases" Supplemental.
Wang et al "Plant Grafting: How Genetic Exchange Promotes Vascular Reconnection" New Phytologist, pp. 1-10, 2016.

* cited by examiner

Second plant tissue (scion)
Crop (Solanaceae, tomato)

First plant tissue (interstock)

Third plant tissue (stock)
Useful root system
(Fabaceae, Cucurbitaceae, etc.)

Fern tissue    Nicotiana tissue

GRAFTED PLANT BODY AND METHOD FOR PRODUCING SAME

CROSS REFERENCE TO RELATED APPLICATIONS

This application is the National Stage of International Application No. PCT/JP2015/079118, filed on Oct. 15, 2015, which claims priority to Japanese Application No. 2014-212889, filed on Oct. 14, 2014. The contents of both applications are hereby incorporated by reference in their entirety.

TECHNICAL FIELD

The present specification relates to a grafted plant body and a method for producing the same.

BACKGROUND ART

Grafting is a technique for surgically joining two or more plants together. Grafting is generally applied to gymnosperms and angiosperms, and is widely used horticulturally and agriculturally. In general, grafting is a technique for producing a plant body that comprises a stock constituting a root part and a scion constituting an aerial part, and that exhibits the excellent abilities of both parts. There are various purposes and methods of grafting. For example, bud mutation and new cultivar of general fruit trees are often propagated by cloning by grafting. Moreover, for vegetables, including Solanaceae and Cucurbitaceae, acquisition of disease resistance and improvement in the quality and productivity of fruits etc. can be achieved using a useful root system by grafting.

Grafting is not applicable to all combinations. Grafting is generally considered to be more easily completed between plants in a closer genetic relationship. Successful grafting is a state in which at least two plant bodies grafted through graft surfaces are alive. In general, grafting is less likely to be completed in the order from the same species, same genus, and same family. Grafting between specific different-family plants is reported (NPL 1 and NPL 2) as an exception; however, grafting is generally considered unable to be completed between different-family plants.

CITATION LIST

Non-Patent Literature

NPL 1: Simon, S. V. Jahrb. wiss. Bot., 1930. 72, 137-160.
NPL 2: Nickell L. G., Science, 1948. 108. 389.

SUMMARY OF INVENTION

Technical Problem

Although grafting was an effective technique in various aspects, there were restrictions such that the usefulness of grafting could not be obtained if plants suitable for the purpose of grafting were not found in related plants.

A phenomenon in which grafting is impossible depending on combination is called graft incompatibility. The graft compatibility of specific combinations can be clearly determined. However, the definition of graft incompatibility is ambiguous, and must rely on years of experience. There is no method for quickly determining graft incompatibility. Furthermore, the mechanism of graft incompatibility itself has hardly been scientifically clarified.

The present specification provides a plant body that uses a novel plant body in which graft incompatibility is avoided or suppressed, a method for producing the same, etc.

Solution to Problem

The present inventor found that a plant tissue of a certain species of plant can avoid or suppress graft incompatibility between plant bodies belonging to different families, thereby completing grafting between different families. The present inventor also found that the plant tissue of this species of plant can avoid or suppress graft incompatibility between plant bodies belonging to a wide range of different families, thereby completing grafting between different families. Further, the present inventor found that the plant tissue of this species can deliver various components to other plant tissues in contact with the plant tissue. Based on these findings, the present invention includes the following means.

Item 1. A graft medium between different-family plants, the graft medium comprising a plant tissue of a plant belonging to the family Solanaceae, Brassicaceae, Lamiaceae, or Orobanchaceae.

Item 2. The graft medium according to item 1, which is a graft medium between different-order plants.

Item 3. The graft medium according to item 1 or 2, wherein the plant tissue is a plant tissue of a plant belonging to the family Solanaceae.

Item 4. The graft medium according to any one of items 1 to 3, wherein the plant tissue is a plant tissue of a plant belonging to the genus *Nicotiana*.

Item 5. A plant tissue comprising two different-family plant tissues grafted through the graft medium according to any one of items 1 to 4.

Item 6. A method for producing a plant tissue, comprising grafting two different-family plant tissues through the graft medium according to any one of items 1 to 4.

Item 7. A plant tissue comprising a plant tissue of a plant belonging to the family Solanaceae, Brassicaceae, Lamiaceae, or Orobanchaceae, and a different-family plant tissue grafted with each other.

Item 8. A plant body comprising the plant tissue according to item 5 or 7.

Item 9. The plant body according to item 8, comprising a plant tissue of cultivar.

Item 10. A method for producing a crop, comprising harvesting a crop from the plant body according to item 9.

Item 11. A method for screening a graft medium between graft-incompatible plants, comprising steps (a) to (c):
(a) grafting a subject plant tissue with a different-family plant tissue;
(b) culturing a plant body obtained in step (a); and
(c) when the plant body does not die after step (b), selecting the subject plant tissue as a graft medium between graft-incompatible plants.

Item 12. A method for screening a graft medium between graft-incompatible plants, comprising steps (d) to (f):
(d) grafting plant tissues of plants belonging to two different families through a subject plant tissue;
(e) culturing a plant body obtained in step (d); and
(f) when the plant body does not die after step (e), selecting the subject plant tissue as a graft medium between graft-incompatible plants.

Item 13. A medium for delivering a useful component to a different-family plant, the medium comprising a plant tissue of a plant belonging to the family Solanaceae, Brassicaceae, Lamiaceae, or Orobanchaceae.

Item 14. A plant tissue comprising the delivery medium according to item 13 grafted with a different-family plant tissue.

Item 15. A plant body comprising the plant tissue according to item 14.

Item 16. A method for producing a plant body to which a useful component is delivered, the method comprising delivering a useful component to the plant body according to item 15 through the delivery medium according to item 13 contained in the plant body.

Advantageous Effects of Invention

The present disclosure can provide a grafted plant body that can avoid or suppress graft incompatibility between, for example, plants belonging to different families using a plant tissue having graft-mediating properties, which enable the plant tissue to mediate different plant tissues etc. to complete grafting between them; and that allows selection of graft elements, such as a stock and a scion, with a high degree of freedom. The present disclosure can also provide a method for producing the same, and the like.

DESCRIPTION OF EMBODIMENTS

The disclosure of the present specification relates to a graft medium, a plant body, methods for producing the same, a method for screening a graft medium, and the like. The present inventor used plants belonging to the genus *Nicotiana* as a scion and a stock to evaluate graft compatibility with various plants. Further, graft compatibility was evaluated in the same manner using, as a scion and a stock, related species of the same genus as the genus *Nicotiana*, and related species of the same family as the genus *Nicotiana*. Moreover, based on these results, when a *Nicotiana* plant tissue was used as an interstock to graft plants that could be grafted with the *Nicotiana* plant as a stock or a scion, even different-family plants, which were graft-incompatible with each other, could be grafted. Specifically, the present inventor found that *Nicotiana* plant tissues could be grafted with various plant tissues while avoiding or suppressing graft incompatibility. As a result, the present inventor found mediating properties that allow grafting between graft-incompatible plants by interposing such a plant tissue while avoiding or suppressing their graft incompatibility. The mediating properties were also found in other plant tissues.

Figure 1A:
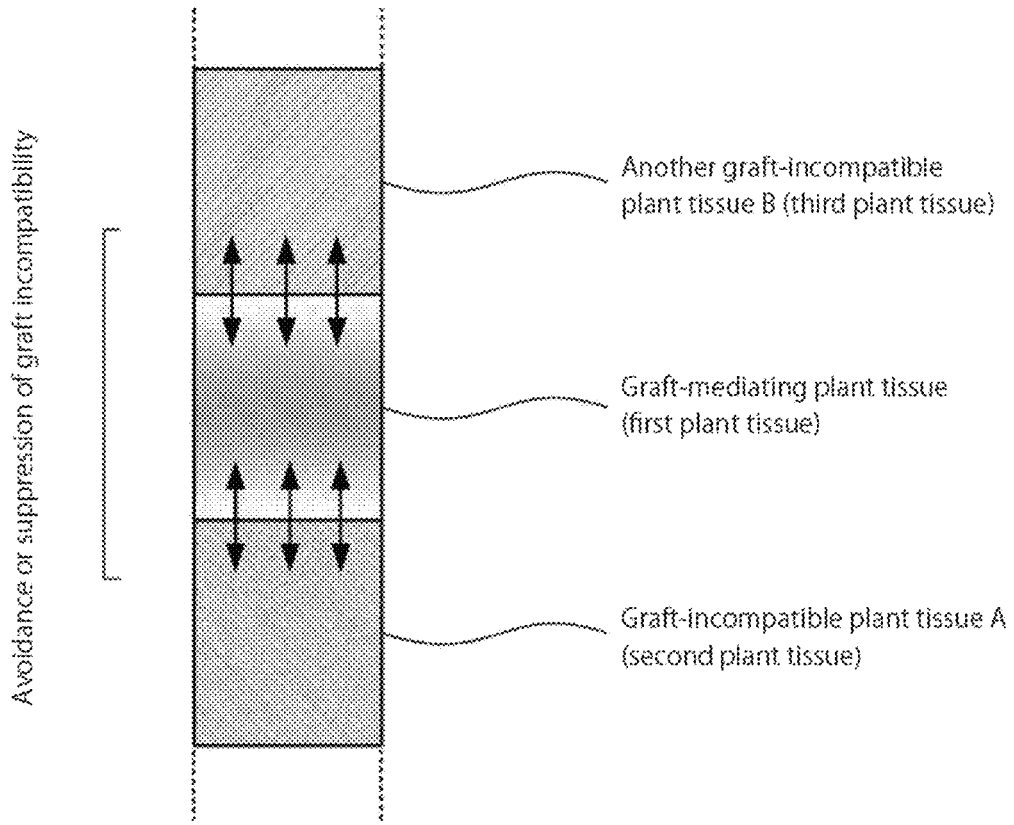
FIG. 1A shows an example of the form of grafting achieved by avoiding or suppressing graft incompatibility using the graft-mediating plant tissue (first plant tissue) of the present disclosure.
Figure 1B:
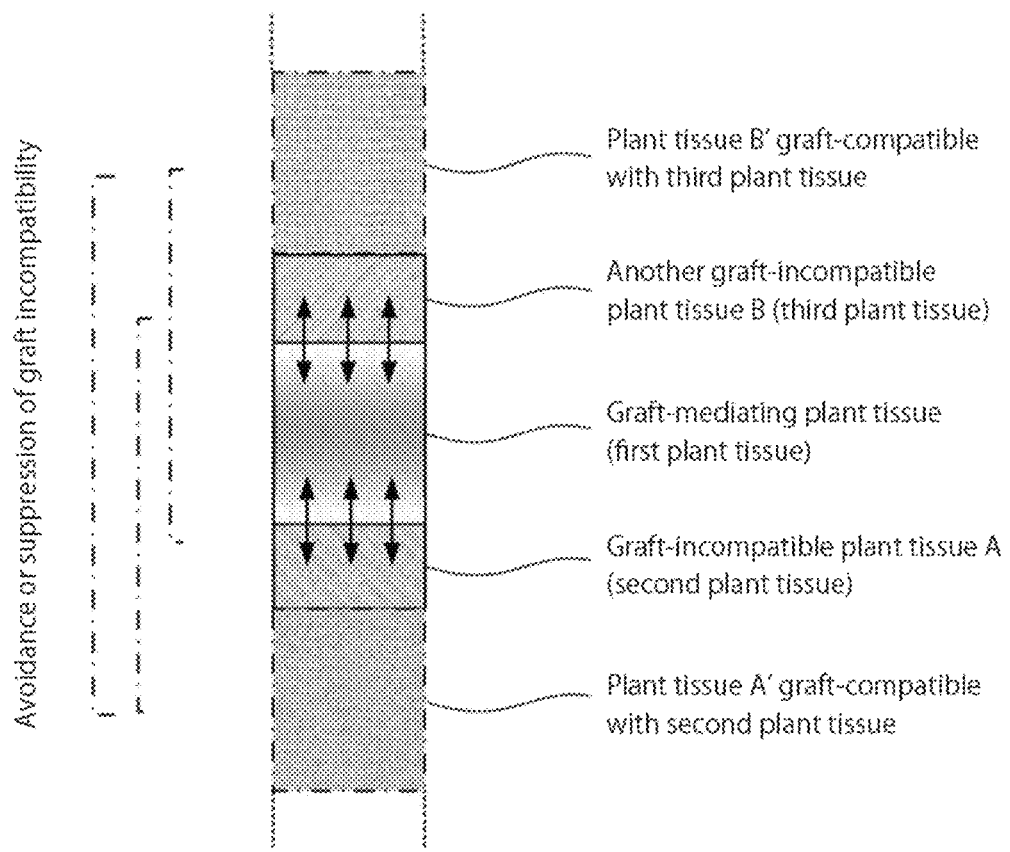
FIG. 1B shows another example of the form of grafting achieved by avoiding or suppressing graft incompatibility using the graft-mediating plant tissue (first plant tissue) of the present disclosure.

FIG. 1 shows the outline of the present disclosure. As shown in FIG. 1A, a graft-mediating plant tissue that can avoid or suppress graft incompatibility allows grafting between plant tissues A and B that belong to different families, or that are originally graft-incompatible but are intended to be grafted with each other, by interposing the plant tissue therebetween. Furthermore, as shown in FIG. 1B, grafting between a plant tissue A and a plant tissue B', which are originally graft-incompatible, but are intended to be grafted with each other, can also be easily completed by interposing a graft-mediating plant tissue and a plant tissue B. For example, even if the graft-mediating plant tissue and the plant tissue B' are less likely to be grafted with each other, the plant tissue B that can be grafted with the graft-mediating plant tissue based on the graft-mediating properties of the plant tissue, and that can also be grafted with the plant tissue B' can be easily prepared. Therefore, the plant tissue A and the plant tissue B' can be consequently grafted with each other. Thus, the graft-mediating plant tissue of the present disclosure can graft plant tissues of a wide range of various plants by direct or gradual grafting.

FIG. 1B similarly shows that grafting between the plant tissue A' and the plant tissue B, and grafting between the plant tissue A' and the plant tissue B' are also possible in the same manner.

The success or failure of grafting of a combination of specific plant tissues depends on the environment, graft site, and treatment. Accordingly, grafting is possible by selecting an environment, graft site, and treatment suitable for plant tissues intended to be grafted. Grafting can be thereby completed between various plant tissues. In consideration of such a background, mediating properties for a wide range of plants (ferns, gymnosperms, and angiosperms that are classified as vascular plants) confirmed by the graft-mediating plant tissue of the present disclosure, and the completion of grafting in various forms as described above, it seems difficult to acknowledge the presence of plants that cannot be grafted by the graft-mediating plant tissue of the present disclosure within the range of ferns, gymnosperms, and angiosperms that are classified as vascular plants.

Furthermore, plant tissues having such mediating properties could deliver one or more useful components to plant bodies through the plant tissues grafted with plant individuals. That is, it was revealed that plant tissues that can mediate graft-incompatible plants can also function as media for transporting or introducing useful components etc. to plant bodies based on the mediating properties described above.

Various embodiments of the present disclosure are described in detail below.

1. Definition

In the present specification, plants mainly refer to vascular plants, and preferably vascular plants.

In the present specification, a plant tissue refers to part of a plant body, and a plant body refers to the entire plant individual (excluding seeds).

In the present specification, the meaning of the term "comprise" includes "essentially consist of" and "consist of."

2. Graft Medium

The present invention relates to a graft medium between different-family plants, the graft medium comprising a plant tissue of a plant belonging to the family Solanaceae, Brassicaceae, Lamiaceae, or Orobanchaceae (also referred to as "the graft medium of the present invention" in the present specification). This is explained below.

The graft medium of the present invention can mediate different-family plants, which generally cannot be grafted with each other, to thereby complete grafting between these different-family plants. As a result, an intended plant tissue 1 of the present invention, and an intended plant body 1 of the present invention, both of which are described later, can be efficiently obtained. Moreover, the graft medium of the present invention also functions as a medium when an additional plant tissue is further added to a plant body comprising one plant tissue 1 of the present invention. Therefore, the graft medium of the present invention can easily obtain plant bodies 1 of the present invention in various forms.

Solanaceae plants are not particularly limited. Examples include plants belonging to the genus *Nicotiana, Anthocercis, Anthotroche, Crenidium, Cyphanthera, Duboisia, Grammosolen, Symonanthus, Petunia, Benthamiella, Bouchetia, Brunfelsia, Combera, Fabiana, Hunzikeria, Leptoglossis, Nierembergia, Pantacantha, Calibrachoa, Plowmania, Capsicum, Lycianthes, Solanum, Jaltomata, Datura, Brugmansia, Physalis, Physaliastrum, Tubocapsicum, Scopolia, Hyoscyamus, Atropa, Mandragora, Lycium, Calibrachoa*, and the like. Among these, in terms of being capable of more efficiently completing grafting between different-family plants when used as a graft medium, preferable are *Nicotiana, Anthocercis, Anthotroche, Crenidium, Cyphanthera, Duboisia, Grammosolen, Symonanthus, Petunia, Benthamiella, Bouchetia, Brunfelsia, Combera, Fabiana, Hunzikeria, Leptoglossis, Nierembergia, Pantacantha, Calibrachoa, Plowmania, Capsicum, Lycianthes, Solanum, Jaltomata*, etc.; more preferable are *Nicotiana, Petunia, Capsicum, Solanum*, etc.; and even more preferable is *Nicotiana*.

Plants belonging to the genus *Nicotiana* are not particularly limited. Examples include *Nicotiana benthamiana, Nicotiana tabacum, Nicotiana umbratica, Nicotiana rustica, Nicotiana acuminata, Nicotiana alata, Nicotiana attenuata, Nicotiana clevelandii, Nicotiana excelsior, Nicotiana forgetiana, Nicotiana glauca, Nicotiana glutinosa, Nicotiana langsdorffii, Nicotiana longiflora, Nicotiana obtusifolia, Nicotiana paniculata, Nicotiana plumbagifolia, Nicotiana quadrivalvis, Nicotiana repanda, Nicotiana suaveolens, Nicotiana sylvestris, Nicotiana tomentosa*, and the like. Among these, in terms of being capable of more efficiently completing grafting between different-family plants when used as a graft medium, preferable are *Nicotiana benthamiana, Nicotiana tabacum, Nicotiana umbratica, Nicotiana rustica*, etc.; and more preferable is *Nicotiana benthamiana*.

Plants belonging to the genus *Petunia* (*Petunia×hybrida*) are not particularly limited. Examples include *Petunia× atkinsiana* (petunia), *Petunia alpicola, Petunia axillaris, Petunia bajeensis, Petunia bonjardinensis, Petunia exserta, Petunia guarapuavensis, Petunia inflata, Petunia integrifolia, Petunia interior, Petunia ledifolia, Petunia littoralis, Petunia mantiqueirensis, Petunia occidentalis, Petunia patagonica, Petunia reitzii, Petunia riograndensis, Petunia saxicola, Petunia scheideana, Petunia villadiana*, and the like. Among these, in terms of being capable of more efficiently completing grafting between different-family plants when used as a graft medium, preferable is *Petunia× atkinsiana*.

Plants belonging to the genus *Capsicum* are not particularly limited. Examples include *Capsicum annuum* L. (e.g., "Grossum" (green pepper), "Abbreviatum," "Acuminoum," "Cerasiforme," "Conoides," "Fasciculatum," "Longum," "Nigrym," "Parvo-acuminatum," etc.), *Capsicum baccatum, Capsicum cardenasii, Capsicum chinense* Jacq. Heser & Smith, *Capsicum frutescens* L., *Capsicum pubescens* Ruiz & Pay., and the like. Among these, in terms of being capable of more efficiently completing grafting between different-family plants when used as a graft medium, preferable is *Capsicum annuum* L., and more preferable is *Capsicum annuum* L. "Grossum" (green pepper).

Plants belonging to the genus *Solanum* are not particularly limited. Examples include *Solanum lycopersicum* L. (tomato), *Solanum melongena* L. (eggplant), *Solanum tuberosum* L., *Solanum acaule* Bitt., *Solanum aethiopicum* L., *Solanum betaceum* Cav., *Solanum jasminoides* Paxt., *Solanum mammosum* L., *Solanum muricatum* Aiton, *Solanum nigrum* L., *Solanum pseudocapsicum* L., *Solanum ptychanthum* Dunal, and the like. Among these, in terms of being capable of more efficiently completing grafting between different-family plants when used as a graft medium, preferable are *Solanum lycopersicum* L. (tomato), *Solanum melongena* L. (eggplant), etc.

Brassicaceae plants are not particularly limited. Examples include plants belonging to the genus *Arabidopsis, Brassica, Capsella, Cardamine, Aethionema, Camelina, Armoracia, Barbarea, Nasturtium, Rorippa, Lepidium, Coronopus, Descurainia, Alyssum, Aurinia, Lobularia, Sisymbrium, Diplotaxis, Eruca, Raphanus, Hirschfeldia, Sinapis, Rapistrum, Orychophragmus, Isatis, Eutrema, Thlaspi, Arabis, Aubrieta, Draba, Macropodium, Noccaea, Iberis, Cochlearia, Malcolmia, Matthiola, Hesperis, Chorispora, Lunaria*, and the like. Among these, in terms of being capable of more efficiently completing grafting between different-family plants when used as a graft medium, preferable are *Arabidopsis, Camelina, Brassica, Diplotaxis, Eruca, Raphanus, Hirschfeldia, Sinapis, Rapistrum, Orychophragmus, Capsella, Cardamine, Armoracia, Barbarea, Nasturtium, Rorippa*, etc.; more preferable are *Arabidopsis, Brassica, Capsella, Cardamine*, etc.; even more preferable are *Arabidopsis, Brassica*, etc.; and still more preferable is *Arabidopsis*.

Plants belonging to the genus *Arabidopsis* are not particularly limited. Examples include *Arabidopsis thaliana, Arabidopsis arenicola, Arabidopsis arenosa, Arabidopsis cebennensis, Arabidopsis croatica, Arabidopsis halleri, Arabidopsis lyrata, Arabidopsis neglecta, Arabidopsis pedemontana, Arabidopsis suecica*, and the like. Among these, in terms of being capable of more efficiently completing grafting between different-family plants when used as a graft medium, preferable is *Arabidopsis thaliana*.

Plants belonging to the genus *Brassica* are not particularly limited. Examples include *Brassica oleracea* (e.g., broccoli, cauliflower, cabbage, etc.), *Brassica napus* (e.g., coleseed etc.), *Brassica barrelieri, Brassica carinata, Brassica elongata, Brassica fruticulosa, Brassica juncea, Brassica narinosa, Brassica nigra, Brassica nipposinica, Brassica rapa, Brassica rupestris, Brassica tournefortii*, and the like.

Among these, in terms of being capable of more efficiently completing grafting between different-family plants when used as a graft medium, preferable are *Brassica oleracea*, *Brassica napus*, etc.; more preferable is *Brassica oleracea*; and even more preferable is broccoli.

Plants belonging to the genus *Capsella* are not particularly limited. Examples include *Capsella rubella*, *Capsella abscissa*, *Capsella andreana*, *Capsella australis*, *Capsella austriaca*, *Capsella bursa-pastoris*, *Capsella divaricata*, *Capsella draboides*, *Capsella gracilis*, *Capsella grandiflora*, *Capsella humistrata*, *Capsella hybrida*, *Capsella hyrcana*, *Capsella integrifolia*, *Capsella lycia*, *Capsella mexicana*, *Capsella orientalis*, *Capsella pillosula*, *Capsella pubens*, *Capsella puberula*, *Capsella schaffneri*, *Capsella stellata*, *Capsella tasmanica*, *Capsella thomsoni*, *Capsella thracica*, *Capsella viguieri*, *Capsella villosula*, and the like. Among these, in terms of being capable of more efficiently completing grafting between different-family plants when used as a graft medium, preferable is *Capsella rubella*.

Plants belonging to the genus *Cardamine* are not particularly limited. Examples include *Cardamine hirsuta*, *Cardamine anemonoides*, *Cardamine appendiculata*, *Cardamine arakiana*, *Cardamine dentipetala*, *Cardamine dentipetala* var. *longifructa*, *Cardamine fallax*, *Cardamine impatiens*, *Cardamine kiusiana*, *Cardamine leucantha*, *Cardamine lyrata*, *Cardamine niigatensis*, *Cardamine nipponica*, *Cardamine pratensis*, *Cardamine regeliana*, *Cardamine schinziana*, *Cardamine scutata*, *Cardamine tanakae*, *Cardamine torrentis*, *Cardamine valida*, and the like. Among these, in terms of being capable of more efficiently completing grafting between different-family plants when used as a graft medium, preferable is *Cardamine hirsuta*.

Lamiaceae plants are not particularly limited. Examples include plants belonging to the genus *Perilla*, *Lavandula*, *Callicarpa*, *Vitex*, *Tectona*, *Premna*, *Ajuga*, *Clerodendrum*, *Caryopteris*, *Amethystea*, *Teucrium*, *Keiskea*, *Elsholtzia*, *Mosla*, *Agastache*, *Nepeta*, *Origanum*, *Mentha*, *Dracocephalum*, *Glechoma*, *Hyssopus*, *Prunella*, *Lycopus*, *Meehania*, *Melissa*, *Monarda*, *Salvia*, *Satureja*, *Rosmarinus*, *Thymus*, *Clinopodium*, *Isodon*, *Hyptis*, *Ocimum*, *Scutellaria*, *Stachys*, *Suzukia*, *Lamium*, *Galeopsis*, *Chelonopsis*, *Pogostemon*, *Leucosceptrum*, *Leonurus*, *Loxocalyx*, *Leucas*, *Marrubium*, and the like. Among these, in terms of being capable of more efficiently completing grafting between different-family plants when used as a graft medium, preferable are *Perilla*, *Lavandula*, *Keiskea*, *Elsholtzia*, *Mosla*, *Agastache*, *Nepeta*, *Origanum*, *Mentha*, *Dracocephalum*, *Glechoma*, *Hyssopus*, *Prunella*, *Lycopus*, *Meehania*, *Melissa*, *Monarda*, *Salvia*, *Satureja*, *Rosmarinus*, *Thymus*, *Clinopodium*, *Isodon*, *Hyptis*, *Ocimum*, etc.; more preferable are *Perilla*, *Lavandula*, etc.; and even more preferable is *Perilla*.

Plants belonging to the genus *Perilla* are not particularly limited. Examples include *Perilla frutescens* (e.g., shiso, sesame, etc.). Among these, in terms of being capable of more efficiently completing grafting between different-family plants when used as a graft medium, preferable is *Perilla frutescens*; and more preferable is shiso.

Plants belonging to the genus *Lavandula* are not particularly limited. Examples include *Lavandula angustifolia* (lavender), *Lavandula latifolia*, *Lavandula stoechas*, *Lavandula multifida*, *Lavandula× intermedia*, and the like. Among these, in terms of being capable of more efficiently completing grafting between different-family plants when used as a graft medium, preferable is *Lavandula angustifolia* (lavender).

Orobanchaceae plants are not particularly limited. Examples include plants belonging to the genus *Phtheirospermum*, *Castilleja*, *Orthocarpus*, *Agalinis*, *Aureolaria*, *Esterhazya*, *Seymeria*, *Lamourouxia*, *Cordylanthus*, *Triphysaria*, *Aeginetia*, *Boschniakia*, *Cistanche*, *Orobanche*, *Phacellanthus*, *Euphrasia*, *Lathraea*, *Melampyrum*, *Monochasma*, *Parentucellia*, *Pedicularis*, *Siphonostegia*, *Striga*, and the like. Among these, in terms of being capable of more efficiently completing grafting between different-family plants when used as a graft medium, preferable are *Phtheirospermum*, *Pedicularis*, *Castilleja*, *Orthocarpus*, *Agalinis*, *Aureolaria*, *Esterhazya*, *Seymeria*, *Lamourouxia*, *Cordylanthus*, *Triphysaria*, etc.; and more preferable is *Phtheirospermum*.

Plants belonging to the genus *Phtheirospenum* are not particularly limited. Examples include *Phtheirospermum japonicum*, *Phtheirospermum glandulosum*, *Phtheirospermum muliense*, *Phtheirospermum parishii*, *Phtheirospermum tenuisectum*, and the like. Among these, in terms of being capable of more efficiently completing grafting between different-family plants when used as a graft medium, preferable is *Phtheirospermum japonicum*.

The form of the graft medium of the present invention is not particularly limited, as long as the medium comprises a plant tissue of a plant belonging to the family Solanaceae, Brassicaceae, Lamiaceae, or Orobanchaceae. The graft medium of the present invention may be a plant body of a plant belonging to the family Solanaceae, Brassicaceae, Lamiaceae, or Orobanchaceae, or may be a form (plant tissue etc.) that is derived from the plant body and promotes the completion of grafting. Moreover, the graft medium of the present invention may comprise only one plant tissue of a plant belonging to the family Solanaceae, Brassicaceae, Lamiaceae, or Orobanchaceae, or two or more of such plant tissues.

Examples of the form of the graft medium of the present invention include a section (plant tissue) of a plant body having surfaces for grafting at both ends (root side and aerial tip side), and a plant body having surfaces for grafting in any two places (root side and aerial tip side). Examples of the surfaces for grafting include cut surfaces in various known forms that allow excellent contact, as necessary, such as flat, concave (e.g., V-shaped), and convex (e.g., projected) surfaces.

Specific examples of the form of the graft medium of the present invention include a stem, petiole, etc. (of a seedling, for example) having surfaces for grafting at both ends, a plant body having surfaces for grafting in any two places of a stem, petiole, etc. (of a seedling, for example). The graft medium of the present invention preferably comprises tissues that undergo active cell activities, such as cell division, for example, parenchyma containing procambium, etc. This is because parenchyma is considered to be able to mediate excellent grafting. Parenchyma refers to a plant tissue composed of parenchyma cells. Examples of parenchyma include cortex and pith of stems and roots, palisade tissue and spongy tissue of leaves, xylem parenchyma and phloem parenchyma of vascular bundles, pulp of fruit, tuber and root tuber, and other storage tissues.

The graft medium of the present invention can be interposed between tissues of two plants belonging to different families (different-family plant tissues) to mediate these plant tissues, thereby completing grafting therebetween. Moreover, the graft medium of the present invention can also complete grafting not only between different-family plants, but also between different-order plants.

In the present specification, the success or failure of grafting between different-family plant tissues can be determined by a graft-completing method and a culture method that are suitable for a plant body from which two different-family plant tissues to be grafted are derived. For example, it can be determined by performing a graft culture test using two different-family plant tissues as a stock and a scion (in some cases, an interstock is interposed between the stock and the scion). As a rule, when the stock and the scion both survive for 4 weeks after grafting, it can be determined that grafting is completed between these plant tissues. When the above conditions are not satisfied, it can be determined that grafting is not completed. The graft completion and the culture test can be performed, for example, in the following manner.

Plants grown in a greenhouse or an artificial weather device using compost are used as a stock and a scion for grafting. Grafting (cleft grafting) is applied to a stem or petiole. A stock is prepared by horizontally cutting a stem or petiole, and making incisions of about 1 to 2 cm in the center of the cut surface. When grafting is applied to a stem, regions between knots are used as much as possible. In addition, when cleft grafting is performed at the position of a stem knot, a stock is prepared by making incisions of about 1 to 2 cm so as to divide between the main stem and a lateral branch or petiole. A scion is prepared by cutting a stem to separate an upper portion, and further cutting the cut end in a V shape so as to fit with the stock. A series of cuts are preferably made using a single-edge shaver. The stem of the scion is gently inserted into the incision made in the stem or petiole of the stock so as not to cause damage, and fixed with parafilm so as to prevent the movement of the scion from that position. A support rod is attached to the stock and the scion, and a plastic bag in which atomized water is sprayed is placed so that the entire scion is covered. Finally, the zip of the plastic bag is closed to a position in which the stem of the stock is located. The stock and the scion are grown in this state for 7 days in an incubator or glass greenhouse at 27° C. under continuous-light conditions with weak light. On the 7th day, an incision is made in the plastic bag, the lower zip is opened, and the stock and the scion are left for another day. On the next day, the plastic bag is removed after it is confirmed that the water inside the plastic bag is volatilized. Thereafter, growing is continued in an incubator or glass greenhouse at 24° C. under continuous-light conditions. When the scion does not die and survives at the fourth week after grafting, grafting is regarded as completed. Moreover, when an interstock is interposed between the stock and the scion, the graft completion and the culture test can be conducted according to the above method.

The graft medium of the present invention can be interposed between two different-family plant tissues to fuse with these plant tissues. This allows intracellular and extracellular transport of useful components, such as components of various plant bodies.

The fusion of the graft medium of the present invention with two different-family plant tissues can be confirmed by morphologically observing these tissues, particularly in a state where the parenchyma of both plants is fused (adhered), using a microscope or the like. Morphological observation can be performed, for example, by resin section observation of a section including the graft surface.

Parenchyma fusion can also be confirmed by evaluating either of the below-mentioned vessel function and sieve tube function of the plant body, in place of, or in combination with, the above morphological observation. For example, the vessel function can be confirmed by detecting the transport of water containing water-soluble dye, such as toluidine blue, from the stock side to the scion side across the graft surface. Further, for example, the sieve tube function can be confirmed by detecting the transport of a fluorochrome (carboxyfluorescein) or the like that serves as an index of symplastic transport through plasmodesmata, from the stock side to the scion side across the graft surface. Moreover, the sieve tube function can be confirmed by detecting the long-distance transport of endogenous mRNA or GFP protein from the stock side to the scion side across the graft surface. Furthermore, taking advantage of the fact that polysaccharide callose accumulated in the cribriform plate of the sieve tube can be visualized by staining with aniline blue, the sieve tube function can be confirmed by detecting the continuous presence of spots of callose across the graft surface. In addition, it can also be confirmed by detecting traces of de novo formation of plasmodesmata in the boundary region of the plant tissues by electron microscope observation of the graft surface.

Plants that are grafted through the graft medium of the present invention are not particularly limited. As is clear from Tables 1 to 11 and FIG. 3, which show plants for which grafting was completed by the graft medium of the present invention, the graft medium of the present invention allows grafting of plant tissues of various plants, including ferns, gymnosperms, angiosperms (magnolias, monocots, and eudicots (eurosids I, eurosids II, euasterids I, euasterids II, and their outgroups)). Specific examples of the plants that are grafted through the graft medium of the present invention include plants belonging to the family Malvaceae, Brassicaceae, Asteraceae, Salicaceae, Ranunculaceae, Lauraceae, Chloranthaceae, Saururaceae, Araceae, Lamiaceae, Violaceae, Umbelliferae, Buxaceae, Ericaceae, Polygonaceae, Amaranthaceae, Convolvulaceae, Rosaceae, Santalaceae, Capparidaceae, Geraniaceae, Vitaceae, Fagaceae, Caprifoliaceae, Dipsacaceae, Fabaceae, Rutaceae, Sapindaceae, Proteaceae, Saxifragaceae, Apocynaceae, Gentianaceae, Aspidiaceae, Cupressaceae, Cucurbitaceae, Solanaceae, Pedaliaceae, Plantaginaceae, Orobanchaceae, Linderniaceae, Capparaceae, Calyceraceae, Goodeniaceae, Menyanthaceae, Stylidiaceae, Polygalaceae, Surianaceae, Muntingiaceae, Cytinaceae, Dipterocarpaceae, Sarcolaenaceae, Cistaceae, Bixaceae, Sphaerosepalaceae, Tetramelaceae, Begoniaceae, Datiscaceae, Berberidaceae, Menispermaceae, Byblidaceae, Stilbaceae, Scrophulariaceae, Mazaceae, Phrymaceae, Paulowniaceae, Piperaceae, Didymellaceae, Hypodematiaceae, Lomariopsis, Nephrolepidaceae, Tectariaceae, Oleandraceae, Polypodiaceae, Davalliaceae, Hypodematiaceae, Lomariopsis, Nephrolepidaceae, Tectariaceae, Oleandraceae, Polypodiaceae, Davalliaceae, and the like. Examples of plants belonging to these families include plants of species evaluated in the Examples.

When a plant tissue of *Nicotiana* of the Solanaceae is used as the graft medium of the present invention, preferable examples of the plants grafted through the graft medium of the present invention include edible plants, including 620 species of 58 families of dicotyledons, 213 species of 20 families of monocotyledons, and 16 species of ferns.

Among the edible plants mentioned above, examples of dicotyledons include 68 species of legumes, such as soybeans, azuki beans, peas, and black-eyed peas; 57 species of cucurbits, such as cucumber, melon, watermelon, and pumpkin; 63 species of solanaceous plants, such as tobacco, eggplant, tomato, and green pepper; 57 species of Asteraceae plants, such as crown daisy, Japanese butterbur, burdock, and lettuce; 24 species of umbellifers, such as carrot, parsley, honewort, and celery; 23 species of Polygonaceae plants, such as sorrel, knotweed, rhubarb, and buckwheat; and 44 species of Amaranthaceae plants, such as spinach, saltwort, Swiss chard, and beet.

Further, among the edible plants mentioned above, examples of monocotyledons include 50 species of Liliaceae plants, 22 species of Araceae plants, 26 species of Dioscorea plants, and 40 species of Poaceae plants. Other examples include arboreous plants, such as Rutaceae and Palmae, and 149 species of 31 families of spices.

When a plant tissue of Solanaceae, such as *Petunia*, *Capsicum*, or *Solanum*, is used as the graft medium of the present invention, preferable examples of the plants grafted through the graft medium of the present invention include plants belonging to the Brassicaceae, Cleomaceae, Capparaceae, Asteraceae, Calyceraceae, Goodeniaceae, Menyanthaceae, Stylidiaceae, Apocynaceae, Gentianaceae, Fabaceae, Polygalaceae, Surianaceae, and the like; and more preferably Brassicaceae, Asteraceae, Apocynaceae, Fabaceae, and the like. Examples of plants belonging to these families include plants of species evaluated in the Examples.

When a plant tissue of Brassicaceae, such as *Arabidopsis*, is used as the graft medium of the present invention, preferable examples of the plants grafted through the graft medium of the present invention include plants belonging to Asteraceae, Calyceraceae, Goodeniaceae, Menyanthaceae, Stylidiaceae, Malvaceae, Muntingiaceae, Cytinaceae, Dipterocarpaceae, Sarcolaenaceae, Cistaceae, Bixaceae, Sphaerosepalaceae, Cucurbitaceae, Tetramelaceae, Begoniaceae, Datiscaceae, Ranunculaceae, Berberidaceae, Menispermaceae, Linderniaceae, Byblidaceae, Stilbaceae, Plantaginaceae, Scrophulariaceae, Lamiaceae, Mazaceae, Phrymaceae, Paulowniaceae, Solanaceae, Convolvulaceae, Fabaceae, Polygalaceae, Surianaceae, Apocynaceae, Gentianaceae, Orobanchaceae, and the like; and more preferably Asteraceae, Malvaceae, Cucurbitaceae, Ranunculaceae, Linderniaceae, Plantaginaceae, Lamiaceae, Solanaceae, Convolvulaceae, Fabaceae, Apocynaceae, and Orobanchaceae. Examples of plants belonging to these families include plants of species evaluated in the Examples.

When a plant tissue of Lamiaceae, such as *Perilla*, is used as the graft medium of the present invention, preferable examples of the plants grafted through the graft medium of the present invention include Brassicaceae, Cleomaceae, Capparaceae, Fabaceae, Polygalaceae, Surianaceae, Asteraceae, Calyceraceae, Goodeniaceae, Menyanthaceae, Stylidiaceae, Cucurbitaceae, Tetramelaceae, Begoniaceae, Datiscaceae, Solanaceae, Convolvulaceae, Saururaceae, Piperaceae, Apocynaceae, Gentianaceae, Buxaceae, Didymellaceae, Orobanchaceae, Mazaceae, Phrymaceae, Paulowniaceae, and the like; and more preferably Brassicaceae, Fabaceae, Asteraceae, Cucurbitaceae, Solanaceae, Saururaceae, Apocynaceae, Buxaceae, Orobanchaceae, and the like. Examples of plants belonging to these families include plants of species evaluated in the Examples.

When a plant tissue of Orobanchaceae, such as *Phtheirospermum*, is used as the graft medium of the present invention, preferable examples of the plants grafted through the graft medium of the present invention include Apocynaceae, Gentianaceae, Asteraceae, Calyceraceae, Goodeniaceae, Menyanthaceae, Stylidiaceae, Fabaceae, Polygalaceae, Surianaceae, Buxaceae, Didymellaceae, Saururaceae, Piperaceae, Aspidiaceae, Hypodematiaceae, Lomariopsis, Nephrolepidaceae, Tectariaceae, Oleandraceae, Polypodiaceae, Davalliaceae, Cucurbitaceae, Tetramelaceae, Begoniaceae, Datiscaceae, Solanaceae, Convolvulaceae, Brassicaceae, Cleomaceae, Capparaceae, and the like; and more preferably Apocynaceae, Asteraceae, Fabaceae, Buxaceae, Saururaceae, Dryopteridaceae, Cucurbitaceae, Solanaceae, Brassicaceae, and the like. Examples of plants belonging to these families include plants of species evaluated in the Examples.

3. Plant Tissue and Plant Body

The present invention relates to:

a plant tissue comprising two different-family plant tissues grafted through the graft medium of the present invention (also referred to as "the plant tissue 1 of the present invention" in the present specification);

a plant body comprising the plant tissue 1 of the present invention (also referred to as "the plant body 1 of the present invention" in the present specification);

a plant tissue comprising a plant tissue of a plant belonging to the family Solanaceae, Brassicaceae, Lamiaceae, or Orobanchaceae grafted with a different-family plant tissue (also referred to as "the plant tissue 2 of the present invention" in the present specification); and a plant body comprising the plant tissue 2 of the present invention (also referred to as "the plant body 2 of the present invention" in the present specification).

These are explained below.

As shown in FIG. 1, the plant tissue 1 of the present invention comprises at least the graft medium of the present invention comprising a plant tissue of a plant belonging to the family Solanaceae, Brassicaceae, Lamiaceae, or Orobanchaceae (a first plant tissue), and tissues of two plants belonging to different families (i.e., graft-incompatible with each other) grafted through the graft medium of the present invention (a second plant tissue and a third plant tissue). The plant body 1 of the present invention may be a plant body consisting of the first plant tissue 1 of the present invention, or, as shown in FIG. 1B, a plant body further comprising, in addition to the plant tissue 1 of the present invention, other plant tissues (a plant tissue A' and a plant tissue B'). Because of grafting mediated by the graft medium of the present invention, the plant tissue 1 of the present invention and the plant body 1 of the present invention can have the various functions of both of the second and third plant tissues, which are originally graft-incompatible with each other, and also have the various functions of the first plant tissue.

The plant tissue 2 of the present invention comprises at least a plant tissue of a plant belonging to the family Solanaceae, Brassicaceae, Lamiaceae, or Orobanchaceae (a first plant tissue), and one plant tissue (a fourth plant tissue) belonging to a family different from that of the first plant tissue and grafted with the first plant tissue (i.e., a plant tissue conventionally graft-incompatible with the first plant tissue). The plant body 2 of the present invention may be a plant body consisting of the plant tissue 2 of the present invention, or a plant body further comprising, in addition to the plant tissue 2 of the present invention, other plant tissues (a plant tissue A' and a plant tissue B'). The plant tissue 2 of the present invention and the plant body 2 of the present invention can have both the various functions of the first plant tissue, and the various functions of the fourth plant tissue, which is conventionally graft-incompatible with the first plant tissue.

Since the plant tissues 1 and 2 of the present invention, and the plant bodies 1 and 2 of the present invention each have a fused area of such different plant tissues, they can also be referred to as grafted plant tissues (grafted plant bodies).

Figure 2:
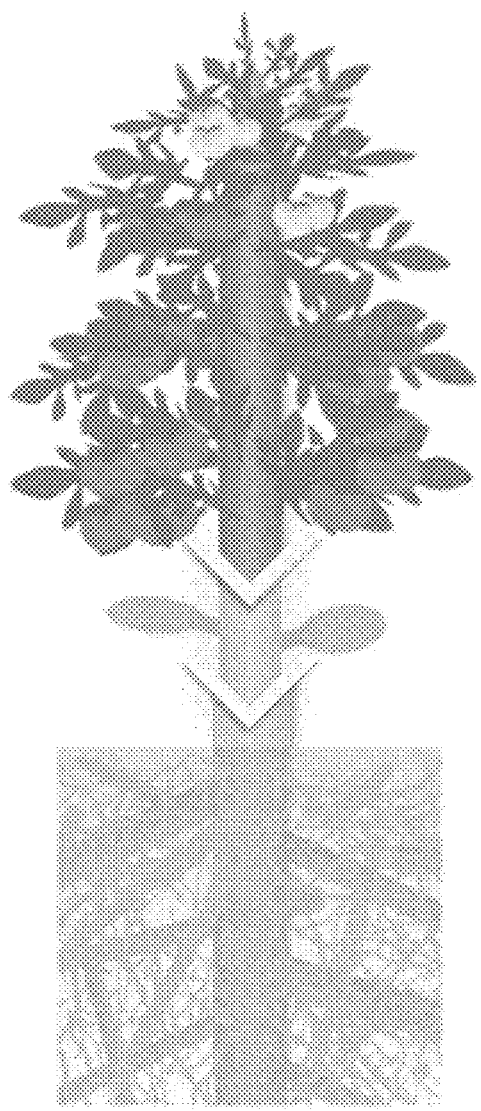
FIG. 2 shows an example of the concept of the grafted plant body of the present disclosure.

A typical embodiment (embodiment 1) of the plant tissue 1 of the present invention and the plant body 1 of the present invention is, for example, as shown in FIG. 2, such that the first plant tissue is an interstock, the third plant tissue (or the second plant tissue) is a stock, and the second plant tissue (or the third plant tissue) is a scion. Another embodiment (embodiment 2) of the plant tissue 1 of the present invention and the plant body 1 of the present invention is, for example, such that a set of the first to third plant tissues is provided on a stock; that is, a stock is provided further on the root side of the plant tissue (the second plant tissue or the third plant tissue) grafted with the root side of the first plant tissue. Still another embodiment (embodiment 3) of the plant tissue 1 of the present invention and the plant body 1 of the present invention is, for example, such that a scion is provided on a set of the first to third plant tissues; that is, a scion is provided further on the aerial tip side of the plant tissue (the second plant tissue or the third plant tissue) grafted with the aerial tip side of the first plant tissue. The additional scion or stock is preferably a plant tissue of a closely related plant highly graft-compatible with the plant tissue to be grafted, or the first plant tissue. Still another embodiment (embodiment 4) of the plant tissue 1 of the present invention and the plant body 1 of the present invention is, for example, a stock and/or a scion are/is further provided on the root side and/or the aerial tip side of a set of the first to third plant tissues through another first plant tissue.

A typical embodiment (embodiment 1) of the plant tissue 2 of the present invention and the plant body 2 of the present invention is, for example, such that the first plant tissue (or the fourth plant tissue) is a stock, and the fourth plant tissue (or the first plant tissue) is a scion. Another embodiment (embodiment 2) of the plant tissue 2 of the present invention and the plant body 2 of the present invention is, for example, such that a set of the first and fourth plant tissues is provided on a stock; that is, a stock is provided further on the root side of the plant tissue (the first plant tissue or the fourth plant tissue) on the root side. Still another embodiment (embodiment 3) of the plant tissue 2 of the present invention and the plant body 2 of the present invention is, for example, such that a scion is provided on a set of the first and fourth plant tissues; that is, a scion is provided further on the aerial tip side of the plant tissue (the first plant tissue or the fourth plant tissue) on the aerial tip side. The additional scion or stock is preferably a plant tissue of a closely related plant highly graft-compatible with the plant tissue to be grafted, or the first plant tissue. Still another embodiment (embodiment 4) of the plant tissue 2 of the present invention and the plant body 2 of the present invention is, for example, such that a stock and/or a scion are/is further provided on the root side and/or the aerial tip side of a set of the first and fourth plant tissues through another first plant tissue.

Further, the plant tissue 1 of the present invention and the plant body 1 of the present invention may comprise a set of the first to third plant tissues in the branch portion of the plant tissues. For example, the second plant tissue and the first plant tissue may be used as the stock and the interstock, respectively, and only the third plant tissue may be provided as the branch portion. Further, for example, the second plant tissue may be used as the stock, and the first and third plant tissues may be provided as the branch portion. This set may be provided entirely as the branch portion of the plant tissues. Similarly, the plant tissue 2 of the present invention and the plant body 2 of the present invention may comprise a set of the first plant tissue and the fourth plant tissue in the branch portion of the plant tissues.

Moreover, in the plant tissue 1 of the present invention and the plant body 1 of the present invention, the plant body may comprise a plurality of sets of the same or different combinations of the first to third plant tissues. The plural sets may comprise opposing plant tissues as plant tissues of related plants with high graft-compatibility, or through the first plant tissue. Similarly, in the plant tissue 2 of the present invention and the plant body 2 of the present invention, the plant body may comprise a plurality of sets of the same or different combinations of the first and fourth plant tissues.

Furthermore, for the plant tissues 1 and 2 of the present invention, and the plant bodies 1 and 2 of the present invention, the various embodiments described above can be suitably combined.

Examples of the first plant tissue (a plant tissue of a plant belonging to the family Solanaceae, Brassicaceae, Lamiaceae, or Orobanchaceae) include the same plant tissues mentioned in the "2. Graft Medium" above.

Examples of the second to fourth plant tissues include plant tissues of the same plants mentioned as examples of the "plants that are grafted through the graft medium of the present invention" in "2. Graft Medium" above.

The second to fourth plant tissues can have a fused area for the graft medium of the present invention or the first plant tissue. The fused area can be derived from the cut surface made on the second to fourth plant tissues. The cut surface of the second to fourth plant tissues are each a site to be in contact with the cut surface of the graft medium of the present invention or the first plant tissue during grafting, and can have a form that can be in contact with the cut surface. As with the graft medium of the present invention or the first plant tissue, examples of the cut surface for grafting include cut surfaces in various known forms that allow excellent contact, as necessary, such as flat, concave (e.g., V-shaped), and convex (e.g., projected) surfaces. The second to fourth plant tissues preferably comprise parenchyma, as with the graft medium of the present invention or the first plant tissue.

For example, when the second to fourth plant tissues are plant tissues including roots, plant tissues of plants having a useful root system (e.g., one showing disease resistance, drought resistance, salt tolerance, base resistance, or acid resistance, or having a useful rhizome part) are selected.

Specific examples include Fabaceae, Cucurbitaceae, Asteraceae, and the like.

Because the plant bodies 1 and 2 of the present invention comprise the graft medium of the present invention or the first plant tissue, grafting can be completed between species for which grafting is conventionally considered to be impossible. Therefore, a highly useful grafted plant body can be provided by selecting the second to fourth plant tissues, depending on the purpose, with a high degree of freedom. From the viewpoint that more excellent crops can be more efficiently produced by taking advantage of this usefulness, it is preferable that the plant bodies 1 and 2 of the present invention comprise a plant tissue of cultivar. In this case, the first to fourth plant tissues may be plant tissues of cultivar, or plant tissues contained in addition to the first to fourth plant tissues may be plant tissues of cultivar. In light of the above, the present invention can also provide a method for producing a crop, comprising harvesting a crop from the plant body 1 or 2 of the present invention.

Specific examples of cultivar include solanums, such as tomato, green pepper, red pepper, and eggplant; cucurbits, such as cucumber, pumpkin, melon, and watermelon; leafy vegetables, such as cabbage, broccoli, and Chinese cabbage; green vegetables and condiment vegetables, such as celery, parsley, and lettuce; alliums, such as Welsh onion, onion, and garlic; legumes, such as soybeans, peanuts, kidney beans, peas, and azuki beans; other fruit vegetables, such as strawberry; axial roots, such as radish, turnip, carrot, and burdock; potatoes, such as taro, cassava, Irish potato, sweet potato, and yam; potherbs, such as asparagus, spinach, and honewort; flowering plants, such as prairie gentian, stock, carnation, and *chrysanthemum*; grains, such as rice and corn; grasses, such as bentgrass and *Zoysia matrella*; oil crops, such as rapeseed and peanut; sugar crops, such as sugar cane and sugar beet; fiber crops, such as cotton and rush; forage crops, such as clover, sorghum, and dent corn; deciduous fruit trees, such as apple, pear, grape, and peach; citrus, such as Satsuma orange, lemon, and grapefruit; arbor, such as satsuki, azalea, and cedar; and the like.

The plant tissue 1 of the present invention and the plant body 1 of the present invention can be obtained by a grafting method comprising grafting tissues of two plants belonging to different families through the graft medium of the present invention. More specifically, the plant tissue 1 of the present invention and the plant body 1 of the present invention can be obtained by a grafting method comprising bringing the second plant tissue (or the third plant tissue) into contact with the root side of the graft medium of the present invention, and the third plant tissue (or the second plant tissue) into contact with the aerial tip side of the graft medium of the present invention. According to this grafting method, intended grafted plant bodies can be efficiently obtained.

The plant tissue 2 of the present invention and the plant body 2 of the present invention can be obtained by a grafting method comprising grafting the first plant tissue and a tissue of one plant belonging to a family different from that of the first plant tissue. More specifically, the plant tissue 2 of the present invention and the plant body 2 of the present invention can be obtained by a grafting method comprising bringing the fourth plant tissue into contact with the root side or aerial tip side of the graft medium of the present invention. According to this grafting method, intended grafted plant bodies can be efficiently obtained.

The contacting step can be carried out using a known grafting method. For example, this step may be carried out using the graft medium of the present invention or the first plant tissue as an interstock, the second plant tissue as a stock, and the third plant tissue as a scion. Further, graft surfaces are closely attached to each other, as appropriate, after connecting treatment, and the connected portion can be suitably supported with a film, an instrument, or the like, as required, so that a closely attached state can be physically formed.

The order of connecting the plant tissues is not particularly specified. All of the plant tissues may be connected at the same period and grown (cultured). Alternatively, the second plant tissue and the graft medium of the present invention may be grown (cultured) in a grafted state, and then the third plant tissue may be added and connected to obtain a connected body. Alternatively, the graft medium of the present invention and the third plant tissue may be grown (cultured) in a grafted state, and then the second plant tissue may be added and connected to obtain a grafted plant body. Alternatively, a grafted body of the second plant tissue and the graft medium of the present invention, and a grafted body of the third plant tissue and the graft medium of the present invention may be separately prepared, and the graft media of the present invention in these grafted bodies may be grafted with each other.

The present invention can also provide a kit for producing the plant tissue 1 of the present invention and the plant body 1 of the present invention, the kit comprising a grafted body comprising the graft medium of the present invention or the first plant tissue as a scion, and the second plant tissue as a stock, and a grafted body comprising the graft medium of the present invention or the first plant tissue as a stock, and the third plant tissue as a scion. Further, the present invention also provides a material for producing the plant tissue 1 of the present invention and the plant body 1 of the present invention, the material comprising any of these grafted bodies, or the graft medium of the present invention. According to the production kit and the production material, the plant tissue 1 of the present invention and the plant body 1 of the present invention can be efficiently obtained.

Similarly, the present invention can also provide a material for producing the plant tissue 2 of the present invention and the plant body 2 of the present invention, the material comprising a scion, stock, or interstock comprising the first plant tissue.

4. Screening Method

The present invention relates to a method for screening a graft medium between graft-incompatible plants, comprising steps (a) to (c):

(a) grafting a subject plant tissue with a different-family plant tissue;

(b) culturing a plant body obtained in step (a); and (c) when the plant body does not die after step (b), selecting the subject plant tissue as a graft medium between graft-incompatible plants (also referred to as "the screening method 1 of the present invention" in the present specification). This is explained below.

The screening method 1 of the present invention is a method for screening a graft medium that can avoid or suppress graft incompatibility between different plants (generally between plants belonging to different families).

Step (a) can be carried out by, for example, producing a grafted seedling using a subject plant tissue as a stock (or a scion), and a tissue of another plant belonging to a family different from that of the subject plant tissue as a scion (or a stock).

The subject plant tissue is a plant tissue that is intended to be used as a graft medium that can also be used as an interstock, i.e., the graft medium of the present invention. For example, when screening is performed, the graft surface is treated as in the first plant tissue mentioned above, the stock or the scion is also treated in the same manner, and these are subjected to the step of producing a grafted seedling. The grafted seedling can be produced by using a known grafting method. The step of producing a grafted seedling can be carried out by using the subject plant tissue as a stock, and two or more other plant tissues as a scion. This step can also be carried out by using the subject plant tissue as a scion, and two or more other plant tissues as a stock. By performing both of them, the graft compatibility and preferable use form of the subject plant tissue can be more reliably determined, and a graft medium can be efficiently screened.

The culture conditions in step (b) are not particularly limited, and can be appropriately set depending on the type of subject plant tissue and the type of plant tissue to be grafted with the subject plant tissue. The culture period is not particularly limited, as long as the success or failure of grafting can be evaluated. The culture period can be appropriately set depending on the type of subject plant tissue and the type of plant tissue to be grafted with the subject plant tissue. The culture period is, for example, 2 to 8 weeks, and preferably 3 to 5 weeks.

The determination of death in step (c) can be conducted according to or substantially according to known standards.

When the plant body does not die, the subject plant tissue can be used as a graft medium between graft-incompatible plants.

More specifically, steps (a) to (c) can be carried out in the same manner, for example, as in the "graft completion and culture test" explained in "2. Graft Medium" above, or as in the Examples.

Further, the present invention relates to a method for screening a graft medium between graft-incompatible plants, comprising steps (d) to (f):

(d) grafting plant tissues of plants belonging to two different families through a subject plant tissue;

(e) culturing a plant body obtained in step (d); and (f) when the plant body does not die after step (e), selecting the subject plant tissue as a graft medium between graft-incompatible plants (also referred to as "the screening method 2 of the present invention" in the present specification). This is explained below.

As with the screening method 1 of the present invention, the screening method 2 of the present invention is a method for screening a graft medium that can avoid or suppress graft incompatibility between different plants (generally between plants belonging to different families). Step (d) can be carried out by, for example, producing a grafted seedling using a subject plant tissue as an interstock, and tissues of plants belonging to different families as a stock and a scion. The step of producing a grafted seedling including an interstock can be performed in place of, or in combination with, the step of producing a grafted seedling having a stock/scion structure described above. By performing the step of producing a grafted seedling including an interstock, the graft compatibility between the stock and the scion can be evaluated in more detail using the subject plant tissue as the interstock. Therefore, a more realistic grafting structure can be efficiently obtained, and a graft medium can be efficiently screened.

A grafted seedling using an interstock can be produced by the previously explained method for producing a grafted plant body.

The culture conditions in step (e) are not particularly limited, and can be appropriately set depending on the type of subject plant tissue and the type of plant tissue to be grafted with the subject plant tissue. The culture period is not particularly limited, as long as the success or failure of grafting can be evaluated. The culture period can be appropriately set depending on the type of subject plant tissue and the type of plant tissue to be grafted with the subject plant tissue. The culture period is, for example, 2 to 8 weeks, and preferably 3 to 5 weeks.

The determination of death in step (f) can be conducted according to or substantially according to known standards. When the plant body does not die, the subject plant tissue can be used as a graft medium between graft-incompatible plants.

The screening methods 1 and 2 of the present invention facilitate the acquisition of a graft medium that can be used as, for example, an interstock useful to efficiently obtain a grafted plant body of the intended purpose by mediating two plants having poor graft compatibility.

5. Useful Component Delivery Medium

The present invention relates to a medium for delivering useful components to a different-family plant, the medium comprising a plant tissue of a plant belonging to the family Solanaceae, Brassicaceae, Lamiaceae, or Orobanchaceae (also referred to as "the useful component delivery medium of the present invention" in the present specification). This is explained below.

According to the useful component delivery medium of the present invention, useful components can be delivered, through the medium, to a plant body belonging to a family different from that of the medium. These useful components allow the control of the various characteristics of the plant body (recipient plant body), such as growth, form, bloom, and fruition; or incentives and control of bacteria using the plant body as a host, microorganisms (e.g., viruses), and animals (e.g., insects). These effects are derived from functional expression of elements, compounds, metabolites, proteins, etc.; post-transcriptional gene silencing (PTGS) by the action of non-coding RNA, such as siRNA or microRNA; or gene silencing (TGS) by genomic DNA modification. Moreover, for the acquisition of the above trait, effects exhibited only in the present generation, and effects inherited by the next generation are both contained.

Examples of the first plant tissue (a plant tissue of a plant belonging to the family Solanaceae, Brassicaceae, Lamiaceae, or Orobanchaceae) in the useful component delivery medium of the present invention include the same plant tissues mentioned in "2. Graft Medium" above. It is known that the first plant tissue can transport, to an adjacent different-family plant tissue, useful components, such as biopolymers (e.g., mRNA and protein) and low-molecular substances (e.g., water-soluble compounds), which are supposed to be mainly transported through the symplastic pathway and, particularly in the case of long-distance transport, are supposed to be mainly transported through sieve tubes; and useful components, such as low-molecular substances (e.g., water-soluble compounds), which are supposed to be mainly transported through the apoplastic pathway and, particularly in the case of long-distance transport, are supposed to be mainly transported through vessels. These useful components allow control of the various characteristics of the recipient plant body.

The form of the graft medium of the present invention is not particularly limited, as long as it comprises a plant tissue of a plant belonging to the family Solanaceae, Brassicaceae, Lamiaceae, or Orobanchaceae. Examples include a plant tissue or plant body having a surface for grafting in any one part. Preferably, a form similar to the form of the graft medium of the present invention mentioned above can be used.

Useful components are not particularly limited. Any components that can be delivered to an adjacent different-family plant tissue can be used. Examples of useful components include non-coding RNA (e.g., siRNA and microRNA), RNA (e.g., mRNA), proteins, various plant hormones, and the like that are supposed to be mainly transported through the symplastic pathway; and elements, metabolites, secretor peptides, proteins, various hormones, and the like that are supposed to be mainly transported through the apoplastic pathway. In addition to components derived from the plant body, drugs, nutritious ingredients, and like components that are not derived from the plant body can also be used as useful components. Certain types of RNA and protein are known to have excellent migratory properties between plant tissues. Migratory properties can be imparted or improved by adding the element of such migrating RNA or protein to desired RNA or protein to form fused RNA or fused protein. Such fused RNA and fused protein can also be used as useful components.

When the useful component delivery medium of the present invention is used, the useful component delivery medium of the present invention may be grafted with a plant body belonging to a different family. The form thereof is not limited. For grafting, a known technique can be applied, in addition to those already explained before. For example, the useful component delivery medium of the present invention may be grafted as a scion with a plant body. With this form, useful components can be delivered through the useful component delivery medium of the present invention. Moreover, as already explained before, the useful component delivery medium of the present invention may also be used as an interstock.

Furthermore, when the useful component delivery medium of the present invention is used, a first plant tissue that can originally produce desired useful components or that is artificially (by a genetic engineering technique) imparted with an ability to produce desired useful components can be used. A person skilled in the art could suitably select plants with a high productivity of desired useful components. A person skilled in the art could also suitably obtain plant bodies imparted with a high productivity of desired useful components by a genetic engineering technique.

In addition, when the useful component delivery medium of the present invention is used, useful components may be injected (introduced) into the first plant tissue from the outside of the plant body. Since the first plant tissue is excellent in delivering various components, even useful components injected from the outside can be delivered to the recipient plant body.

According to such a use form, the useful component delivery medium of the present invention can be used as a delivery means in such a manner that the medium is grafted with any site of the recipient plant body. As a result, more effective delivery of useful components can be attained.

Further, when the useful component delivery medium of the present invention is used, useful components may be injected (introduced) into a site, other than the first plant tissue, of the plant body. Because the first plant tissue can mediate useful components, useful components injected into a site other than the first plant tissue can also be delivered to other sites of the plant body through the first plant tissue. Examples of the site other than the first plant tissue are not particularly limited. The site may be in the vicinity of the first plant tissue, or a distant part suitable for, for example, injection of useful components. Furthermore, when the plant body comprises any of a general stock, scion, and interstock, the site may be any of them.

According to such a use form, highly useful plant bodies of perennial plants, such as arbor, for which generational change takes a long time, can be obtained more quickly than before.

According to the above explanation, the present invention also provides a method for delivering useful components to a different-family plant using the useful component delivery medium of the present invention. Further, the present invention provides a plant tissue comprising the useful component delivery medium of the present invention grafted with a different-family plant tissue, a plant body comprising the plant tissue, and methods for producing the plant tissue and the plant body.

Furthermore, the present invention provides a method for producing a plant body to which useful components are delivered, the method comprising delivering the useful components through the useful component delivery medium of the present invention. The meaning of the term "through" as used herein is not particularly limited, as long as useful components injected (introduced) into the plant body are delivered to other sites of the plant body mediated by the useful component delivery medium of the present invention. Accordingly, useful components may be delivered by injecting (introducing) the useful components into the useful component delivery medium of the present invention, or by injecting (introducing) the useful components into a site other than the useful component delivery medium of the present invention. Alternatively, useful components may be delivered by obtaining a plant body comprising the useful component delivery medium of the present invention by, for example, grafting a plant tissue that already contains useful components, which may be the useful component delivery medium of the present invention, or a plant tissue other than the delivery medium.

EXAMPLES

The disclosure of the present specification is explained in detail below with reference to Examples. The following Examples are provided to explain the present disclosure, but do not limit the present disclosure.

Example 1

Production of Two-Species Grafted Plant Body

Figure 3:
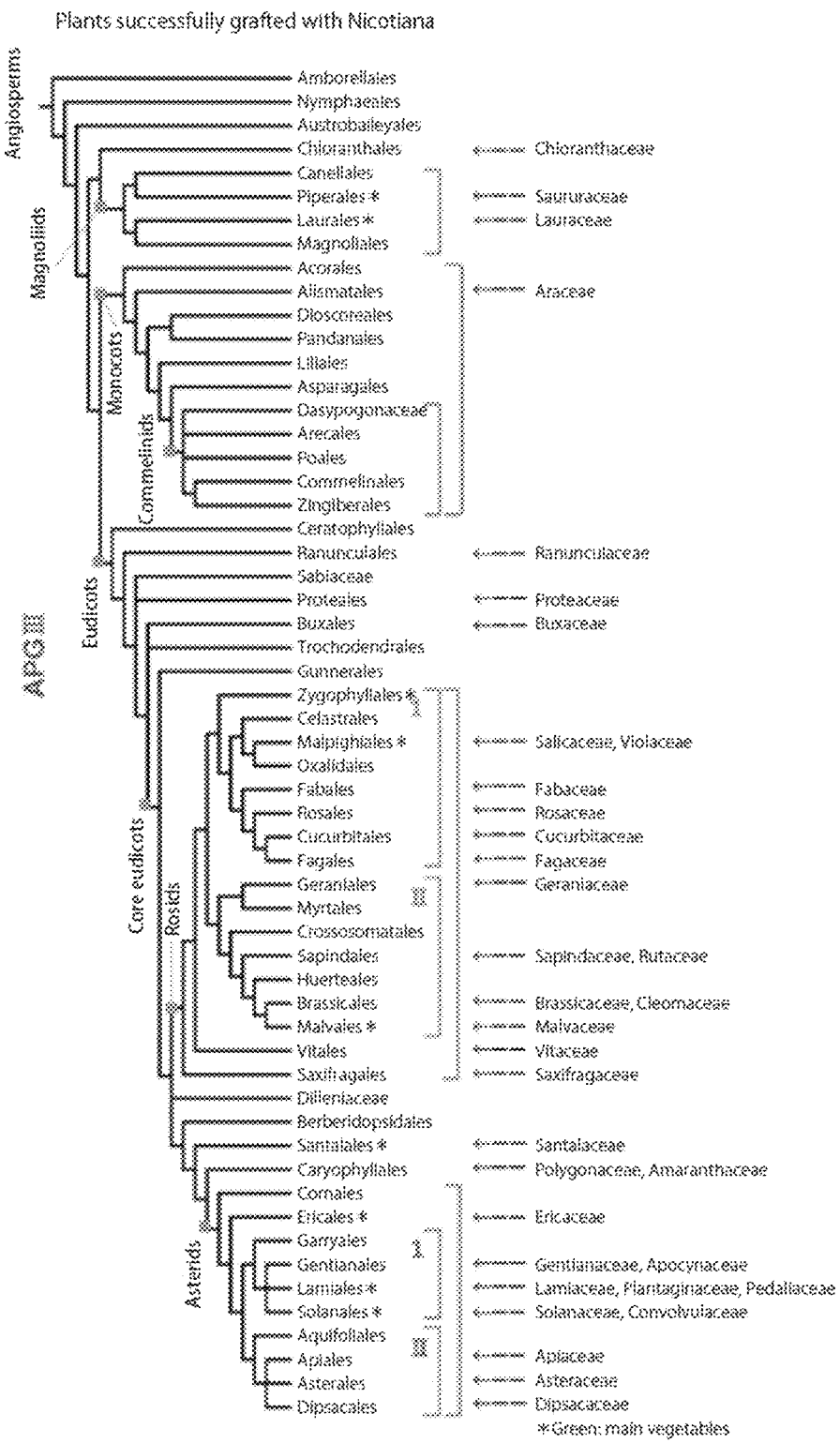
FIG. 3 shows plants successfully grafted with tissues of plants belonging to the genus *Nicotiana* on the Angiosperm Phylogeny Group.

Plants grown in a greenhouse or an artificial weather device using compost were used for grafting. For *Nicotiana benthamiana*, individuals within one to two months after seeding were used, and for other plants, buds or plant seedlings grown for several weeks to several years were used. Grafting (cleft grafting) was applied to a stem or petiole. A stock was prepared by horizontally cutting a stem or petiole, and making incisions of about 1 to 2 cm in the center of the cut surface. When grafting was applied to a stem, regions between knots were used as much as possible. In addition, when cleft grafting was performed at the position of a stem knot, a stock was prepared by making incisions of about 1 to 2 cm so as to divide between the main stem and a lateral branch or petiole. A scion was prepared by cutting a stem to separate an upper portion, and further cutting the cut end in a V shape so as to fit with the stock. A series of cuts were made using a single-edge shaver. The stem of the scion was gently inserted into the incision made in the stem or petiole of the stock so as not to give damage, and fixed with parafilm so as to prevent the movement of the scion from that position. A support rod was attached to the stock and the scion, and a plastic bag in which atomized water was sprayed was placed so that the entire scion was covered. Finally, the zip of the plastic bag was closed to a position in which the stem of the stock was located. The stock and the scion were grown in this state for 7 days in an incubator or glass greenhouse at 27° C. under continuous-light conditions with weak light. On the 7th day, an incision was made in the plastic bag, the lower zip was opened, and the stock and the scion were left for another day. On the next day, the plastic bag was removed after it was confirmed that the water inside the plastic bag was volatilized. Thereafter, growing was continued in an incubator or glass greenhouse at 24° C. under continuous-light conditions. When the scion did not die and survived at the fourth week after grafting, grafting was regarded as completed. The plant culture conditions, the method of grafting (cleft grafting), the growing method after grafting, and the determination of the completion of grafting were the same in the following grafting methods. Tables 1 to 9 show the results. Further, FIG. 3 shows plants successfully grafted with tissues of plants belonging to the genus *Nicotiana* on the Angiosperm Phylogeny Group.

TABLE 1

| Scion | | | | Stock | | | |
| --- | --- | --- | --- | --- | --- | --- | --- |
| Order | Family | Genus | Species | Order | Family | Genus | Species |
| Solanales | Solanaceae | *Nicotiana* | *N. benthamiana* | Apiales | Apiaceae | *Cryptotaenia* | Honeywort |
| Solanales | Solanaceae | *Nicotiana* | *N. benthamiana* | Apiales | Apiaceae | *Daucus* | Carrot |
| Solanales | Solanaceae | *Nicotiana* | *N. benthamiana* | Arales | Araceae | *Anthurium* | Anthurium |
| Solanales | Solanaceae | *Nicotiana* | *N. benthamiana* | Asterales | Asteraceae | *Callistephus* | *C. chinensis* |
| Solanales | Solanaceae | *Nicotiana* | *N. benthamiana* | Asterales | Asteraceae | *Chrysanthemum* | Chrysanthemum |
| Solanales | Solanaceae | *Nicotiana* | *N. benthamiana* | Brassicales | Capparaceae | *Cleome* | Cleome |
| Solanales | Solanaceae | *Nicotiana* | *N. benthamiana* | Buxales | Buxaceae | *Pachysandra* | *P. terminalis* |
| Solanales | Solanaceae | *Nicotiana* | *N. benthamiana* | Caryophyllales | Amaranthaceae | *Alternanthera* | *A. porrigens* |
| Solanales | Solanaceae | *Nicotiana* | *N. benthamiana* | Caryophyllales | Amaranthaceae | *Spinacia* | Spinach |
| Solanales | Solanaceae | *Nicotiana* | *N. benthamiana* | Caryophyllales | Polygonaceae | *Fallopia* | *F. japonica* |
| Solanales | Solanaceae | *Nicotiana* | *N. benthamiana* | Chloranthales | Chloranthaceae | *Sarcandra* | *S. glabra* |
| Solanales | Solanaceae | *Nicotiana* | *N. benthamiana* | Cucurbitales | Cucurbitaceae | *Cucumis* | Cucumber |
| Solanales | Solanaceae | *Nicotiana* | *N. benthamiana* | Dipsacales | Caprifoliaceae | *Abelia* | *A. spathulata* |
| Solanales | Solanaceae | *Nicotiana* | *N. benthamiana* | Dipsacales | Dipsacaceae | *Scabiosa* | *S. atropurpurea* |
| Solanales | Solanaceae | *Nicotiana* | *N. benthamiana* | Ericales | Ericaceae | *Rhododendron* | Azalea |
| Solanales | Solanaceae | *Nicotiana* | *N. benthamiana* | Ericales | Ericaceae | *Vaccinium* | Blueberry |
| Solanales | Solanaceae | *Nicotiana* | *N. benthamiana* | Fabales | Fabaceae | *Glycine* | Soybean |
| Solanales | Solanaceae | *Nicotiana* | *N. benthamiana* | Fabales | Fabaceae | *Medicago* | Alfalfa |
| Solanales | Solanaceae | *Nicotiana* | *N. benthamiana* | Fabales | Fabaceae | *Melilotus* | Melilot |
| Solanales | Solanaceae | *Nicotiana* | *N. benthamiana* | Fabales | Fabaceae | *Pisum* | Pea |
| Solanales | Solanaceae | *Nicotiana* | *N. benthamiana* | Fabales | Fabaceae | *Trifolium* | Clover |
| Solanales | Solanaceae | *Nicotiana* | *N. benthamiana* | Fabales | Fabaceae | *Trigonella* | Fenugreek |
| Solanales | Solanaceae | *Nicotiana* | *N. benthamiana* | Fabales | Fabaceae | *Vicia* | Broad bean |
| Solanales | Solanaceae | *Nicotiana* | *N. benthamiana* | Fabales | Fabaceae | *Vigna* | Azuki bean |
| Solanales | Solanaceae | *Nicotiana* | *N. benthamiana* | Fagales | Fagaceae | *Quercus* | *Q. acutissima* |
| Solanales | Solanaceae | *Nicotiana* | *N. benthamiana* | Fagales | Fagaceae | *Quercus* | *Q. crispula* |
| Solanales | Solanaceae | *Nicotiana* | *N. benthamiana* | Gentianales | Apocynaceae | *Vinca* | *V. major* |
| Solanales | Solanaceae | *Nicotiana* | *N. benthamiana* | Gentianales | Gentianaceae | *Eustoma* | *E. grandiflorum* |
| Solanales | Solanaceae | *Nicotiana* | *N. benthamiana* | Gentianales | Gentianaceae | *Gentiana* | Gentian |
| Solanales | Solanaceae | *Nicotiana* | *N. benthamiana* | Geraniales | Geraniaceae | *Geranium* | Geranium |
| Solanales | Solanaceae | *Nicotiana* | *N. benthamiana* | Lamiales | Pedaliaceae | *Sesamum* | Sesame |
| Solanales | Solanaceae | *Nicotiana* | *N. benthamiana* | Lamiales | Plantaginaceae | *Antirrhinum* | *A. majus* |
| Solanales | Solanaceae | *Nicotiana* | *N. benthamiana* | Laurales | Lauraceae | *Cinnamomum* | *C. camphora* |
| Solanales | Solanaceae | *Nicotiana* | *N. benthamiana* | Malpighiales | Salicaceae | *Populus* | White poplar |
| Solanales | Solanaceae | *Nicotiana* | *N. benthamiana* | Malpighiales | Salicaceae | *Salix* | *Salix matsudana* var. *tortuosa* |
| Solanales | Solanaceae | *Nicotiana* | *N. benthamiana* | Malpighiales | Violaceae | *Viola* | Pansy |
| Solanales | Solanaceae | *Nicotiana* | *N. benthamiana* | Malvales | Malvaceae | *Gossypium* | Cotton |
| Solanales | Solanaceae | *Nicotiana* | *N. benthamiana* | Malvales | Malvaceae | *Pachira* | Pachira |
| Solanales | Solanaceae | *Nicotiana* | *N. benthamiana* | Pinales | Cupressaceae | *Chamaecyparis* | *C. obtusa* |
| Solanales | Solanaceae | *Nicotiana* | *N. benthamiana* | Piperales | Saururaceae | *Houttuynia* | *H. cordata* |
| Solanales | Solanaceae | *Nicotiana* | *N. benthamiana* | Polypodiales | Dryopteridaceae | *Cyrtomium* | *C. fortunei* |
| Solanales | Solanaceae | *Nicotiana* | *N. benthamiana* | Proteales | Proteaceae | *Grevillea* | Grevillea |
| Solanales | Solanaceae | *Nicotiana* | *N. benthamiana* | Ranunculales | Ranunculaceae | *Anemone* | Anemone |
| Solanales | Solanaceae | *Nicotiana* | *N. benthamiana* | Ranunculales | Ranunculaceae | *Consolida* | *C. ajacis* |
| Solanales | Solanaceae | *Nicotiana* | *N. benthamiana* | Rosales | Rosaceae | *Fragaria* | Strawberry |
| Solanales | Solanaceae | *Nicotiana* | *N. benthamiana* | Rosales | Rosaceae | *Malus* | Apple |
| Solanales | Solanaceae | *Nicotiana* | *N. benthamiana* | Rosales | Rosaceae | *Rosa* | Miniature rose |
| Solanales | Solanaceae | *Nicotiana* | *N. benthamiana* | Santalales | Santalaceae | *Buckleya* | *B. lanceolata* |
| Solanales | Solanaceae | *Nicotiana* | *N. benthamiana* | Sapindales | Rutaceae | *Citrus* | Orange |
| Solanales | Solanaceae | *Nicotiana* | *N. benthamiana* | Sapindales | Sapindaceae | *Cardiospermum* | *C. halicacabum* |
| Solanales | Solanaceae | *Nicotiana* | *N. benthamiana* | Saxifragales | Saxifragaceae | *Heucherella* | Heucherella |
| Solanales | Solanaceae | *Nicotiana* | *N. benthamiana* | Solanales | Convolvulaceae | *Ipomoea* | Morning glory |
| Solanales | Solanaceae | *Nicotiana* | *N. benthamiana* | Vitales | Vitaceae | *Vitis* | *V. coignetiae* |
| Solanales | Solanaceae | *Nicotiana* | *N. benthamiana* | Fabales | Fabaceae | *Arachis* | Peanut |
| Solanales | Solanaceae | *Nicotiana* | *N. benthamiana* | Fabales | Fabaceae | *Lotus* | *L Burttii* |
| Solanales | Solanaceae | *Nicotiana* | *N. benthamiana* | Asterales | Asteraceae | *Stevia* | Stevia |
| Solanales | Solanaceae | *Nicotiana* | *N. rustica* | Fabales | Fabaceae | *Glycine* | Soybean |
| Solanales | Solanaceae | *Nicotiana* | *N. tabacum* | Brassicales | Brassicaceae | *Cardamine* | *C. hirsuta* |
| Solanales | Solanaceae | *Nicotiana* | *N. tabacum* | Cucurbitales | Cucurbitaceae | *Cucumis* | Cucumber |
| Solanales | Solanaceae | *Nicotiana* | *N. tabacum* | Cucurbitales | Cucurbitaceae | *Cucurbita* | Pumpkin |
| Solanales | Solanaceae | *Nicotiana* | *N. tabacum* | Fabales | Fabaceae | *Glycine* | Soybean |
| Solanales | Solanaceae | *Nicotiana* | *N. umbratica* | Fabales | Fabaceae | *Glycine* | Soybean |
| Solanales | Solanaceae | *Nicotiana* | *N. benthamiana* | Brassicales | Brassicaceae | *Arabidopsis* | *A. thaliana* (Col) |
| Solanales | Solanaceae | *Nicotiana* | *N. benthamiana* | Brassicales | Brassicaceae | *Brassica* | Coleseed |
| Solanales | Solanaceae | *Nicotiana* | *N. benthamiana* | Brassicales | Brassicaceae | *Brassica* | Cauliflower |
| Solanales | Solanaceae | *Nicotiana* | *N. benthamiana* | Brassicales | Brassicaceae | *Brassica* | Cabbage |
| Solanales | Solanaceae | *Nicotiana* | *N. benthamiana* | Brassicales | Brassicaceae | *Brassica* | Broccoli |
| Solanales | Solanaceae | *Nicotiana* | *N. benthamiana* | Brassicales | Brassicaceae | *Capsella* | *C. rubella* |
| Solanales | Solanaceae | *Nicotiana* | *N. benthamiana* | Brassicales | Brassicaceae | *Cardamine* | *C. hirsuta* |
| Solanales | Solanaceae | *Nicotiana* | *N. benthamiana* | Lamiales | Lamiaceae | *Lavandula* | Lavender |
| Solanales | Solanaceae | *Nicotiana* | *N. benthamiana* | Lamiales | Lamiaceae | *Perilla* | Shiso |
| Solanales | Solanaceae | *Nicotiana* | *N. benthamiana* | Lamiales | Orobanchaceae | *Phtheirospermum* | *P. japonicum* |
| Solanales | Solanaceae | *Nicotiana* | *N. benthamiana* | Solanales | Solanaceae | *Capsicum* | Green pepper |

TABLE 1-continued

| Scion | | | | Stock | | | |
|---|---|---|---|---|---|---|---|
| Order | Family | Genus | Species | Order | Family | Genus | Species |
| Solanales | Solanaceae | *Nicotiana* | *N. benthamiana* | Solanales | Solanaceae | *Nicotiana* | *N. benthamiana* |
| Solanales | Solanaceae | *Nicotiana* | *N. benthamiana* | Solanales | Solanaceae | *Solanum* | Micro-Tom |

TABLE 2

| Scion | | | | Stock | | | |
|---|---|---|---|---|---|---|---|
| Order | Family | Genus | Species | Order | Family | Genus | Species |
| Solanales | Solanaceae | *Petunia* | *Petunia* | Asterales | Asteraceae | *Callistephus* | *C. chinensis* |
| Solanales | Solanaceae | *Petunia* | *Petunia* | Asterales | Asteraceae | *Chrysanthemum* | Chrysanthemum |
| Solanales | Solanaceae | *Petunia* | *Petunia* | Gentianales | Apocynaceae | *Vinca* | *V. major* |
| Solanales | Solanaceae | *Petunia* | *Petunia* | Asterales | Asteraceae | *Stevia* | Stevia |
| Solanales | Solanaceae | *Petunia* | *Petunia* | Brassicales | Brassicaceae | *Arabidopsis* | *A. thaliana* (Col) |
| Solanales | Solanaceae | *Petunia* | *Petunia* | Brassicales | Brassicaceae | *Brassica* | Cabbage |
| Solanales | Solanaceae | *Petunia* | *Petunia* | Brassicales | Brassicaceae | *Brassica* | Broccoli |
| Solanales | Solanaceae | *Capsicum* | Green pepper | Asterales | Asteraceae | *Glebionis* | Crown daisy |
| Solanales | Solanaceae | *Capsicum* | Green pepper | Brassicales | Brassicaceae | *Arabidopsis* | *A. thaliana* (Col) |
| Solanales | Solanaceae | *Solanum* | Ponderosa tomato | Fabales | Fabaceae | *Glycine* | Soybean |
| Solanales | Solanaceae | *Solanum* | Ponderosa tomato | Fabales | Fabaceae | *Vigna* | Azuki bean |
| Solanales | Solanaceae | *Solanum* | Micro-Tom | Asterales | Asteraceae | *Chrysanthemum* | Chrysanthemum |
| Solanales | Solanaceae | *Solanum* | Micro-Tom | Fabales | Fabaceae | *Glycine* | Soybean |
| Solanales | Solanaceae | *Solanum* | Micro-Tom | Brassicales | Brassicaceae | *Arabidopsis* | *A. thaliana* (Col) |
| Solanales | Solanaceae | *Solanum* | Eggplant | Brassicales | Brassicaceae | *Arabidopsis* | *A. thaliana* (Col) |
| Solanales | Solanaceae | *Solanum* | Micro-Tom | Solanales | Solanaceae | *Nicotiana* | *N. benthamiana* |
| Solanales | Solanaceae | *Solanum* | Ponderosa tomato | Solanales | Solanaceae | *Solanum* | Ponderosa tomato |

TABLE 3

| Scion | | | | Stock | | | |
|---|---|---|---|---|---|---|---|
| Order | Family | Genus | Species | Order | Family | Genus | Species |
| Arales | Araceae | *Anthurium* | Anthurium | Solanales | Solanaceae | *Nicotiana* | *N. benthamiana* |
| Asterales | Asteraceae | *Chrysanthemum* | Chrysanthemum | Solanales | Solanaceae | *Nicotiana* | *N. benthamiana* |
| Cucurbitales | Cucurbitaceae | *Cucumis* | Cucumber | Solanales | Solanaceae | *Nicotiana* | *N. benthamiana* |
| Gentianales | Apocynaceae | *Vinca* | *V. major* | Solanales | Solanaceae | *Nicotiana* | *N. benthamiana* |
| Rosales | Rosaceae | *Fragaria* | Strawberry | Solanales | Solanaceae | *Nicotiana* | *N. benthamiana* |
| Sapindales | Rutaceae | *Citrus* | Orange | Solanales | Solanaceae | *Nicotiana* | *N. benthamiana* |
| Vitales | Vitaceae | *Vitis* | *V. coignetiae* | Solanales | Solanaceae | *Nicotiana* | *N. benthamiana* |
| Brassicales | Brassicaceae | *Brassica* | Broccoli | Solanales | Solanaceae | *Nicotiana* | *N. benthamiana* |
| Lamiales | Lamiaceae | *Lavandula* | Lavender | Solanales | Solanaceae | *Nicotiana* | *N. benthamiana* |
| Lamiales | Orobanchaceae | *Phtheirospermum* | *P. japonicum* | Solanales | Solanaceae | *Nicotiana* | *N. benthamiana* |

TABLE 4

| Scion | | | | Stock | | | |
|---|---|---|---|---|---|---|---|
| Order | Family | Genus | Species | Order | Family | Genus | Species |
| Brassicales | Brassicaceae | *Brassica* | Broccoli | Cucurbitales | Cucurbitaceae | *Cucumis* | Cucumber |
| Brassicales | Brassicaceae | *Brassica* | Broccoli | Asterales | Asteraceae | *Chrysanthemum* | Chrysanthemum |
| Brassicales | Brassicaceae | *Brassica* | Broccoli | Solanales | Solanaceae | *Nicotiana* | *N. benthamiana* |
| Brassicales | Brassicaceae | *Brassica* | Broccoli | Brassicales | Brassicaceae | *Brassica* | Broccoli |
| Brassicales | Brassicaceae | *Arabidopsis* | *A. thaliana* (Col) | Brassicales | Brassicaceae | *Capsella* | *C. rubella* |
| Brassicales | Brassicaceae | *Arabidopsis* | *A. thaliana* (Col) | Brassicales | Brassicaceae | *Arabidopsis* | *A. thaliana* (Col) |

TABLE 5

| Scion | | | | Stock | | | |
|---|---|---|---|---|---|---|---|
| Order | Family | Genus | Species | Order | Family | Genus | Species |
| Cucurbitales | Cucurbitaceae | *Citrullus* | Watermelon | Brassicales | Brassicaceae | *Arabidopsis* | *A. thaliana* (Col) |
| Cucurbitales | Cucurbitaceae | *Cucumis* | Cucumber | Brassicales | Brassicaceae | *Arabidopsis* | *A. thaliana* (Col) |
| Fabales | Fabaceae | *Glycine* | Soybean | Brassicales | Brassicaceae | *Arabidopsis* | *A. thaliana* (Col) |
| Fabales | Fabaceae | *Vigna* | Azuki bean | Brassicales | Brassicaceae | *Arabidopsis* | *A. thaliana* (Col) |

TABLE 5-continued

| Scion | | | | Stock | | | |
|---|---|---|---|---|---|---|---|
| Order | Family | Genus | Species | Order | Family | Genus | Species |
| Gentianales | Apocynaceae | *Catharanthus* | *C. roseus* | Brassicales | Brassicaceae | *Arabidopsis* | *A. thaliana* (Col) |
| Lamiales | Linderniaceae | *Torenia* | Bluewings | Brassicales | Brassicaceae | *Arabidopsis* | *A. thaliana* (Col) |
| Lamiales | Plantaginaceae | *Antirrhinum* | *A. majus* | Brassicales | Brassicaceae | *Arabidopsis* | *A. thaliana* (Col) |
| Malvales | Malvaceae | *Abelmoschus* | Okra | Brassicales | Brassicaceae | *Arabidopsis* | *A. thaliana* (Col) |
| Malvales | Malvaceae | *Pachira* | Pachira | Brassicales | Brassicaceae | *Arabidopsis* | *A. thaliana* (Col) |
| Ranunculales | Ranunculaceae | *Consolida* | *C. ajacis* | Brassicales | Brassicaceae | *Arabidopsis* | *A. thaliana* (Col) |
| Solanales | Convolvulaceae | *Ipomoea* | Morning glory | Brassicales | Brassicaceae | *Arabidopsis* | *A. thaliana* (Col) |
| Solanales | Solanaceae | *Capsicum* | Green pepper | Brassicales | Brassicaceae | *Arabidopsis* | *A. thaliana* (Col) |
| Solanales | Solanaceae | *Nicotiana* | *N. benthamiana* | Brassicales | Brassicaceae | *Arabidopsis* | *A. thaliana* (Col) |
| Solanales | Solanaceae | *Petunia* | Petunia | Brassicales | Brassicaceae | *Arabidopsis* | *A. thaliana* (Col) |
| Solanales | Solanaceae | *Solanum* | Micro-Tom | Brassicales | Brassicaceae | *Arabidopsis* | *A. thaliana* (Col) |
| Solanales | Solanaceae | *Solanum* | Eggplant | Brassicales | Brassicaceae | *Arabidopsis* | *A. thaliana* (Col) |
| Lamiales | Lamiaceae | *Perilla* | Shiso, green perilla | Brassicales | Brassicaceae | *Arabidopsis* | *A. thaliana* (Col) |
| Lamiales | Orobanchaceae | *Phtheirospermum* | *P. japonicum* | Brassicales | Brassicaceae | *Arabidopsis* | *A. thaliana* (Col) |
| Brassicales | Brassicaceae | *Capsella* | *C. rubella* | Brassicales | Brassicaceae | *Arabidopsis* | *A. thaliana* (Col) |
| Brassicales | Brassicaceae | *Cardamine* | *C. hirsuta* | Brassicales | Brassicaceae | *Arabidopsis* | *A. thaliana* (Col) |
| Solanales | Solanaceae | *Nicotiana* | *N. benthamiana* | Brassicales | Brassicaceae | *Brassica* | Coleseed |
| Solanales | Solanaceae | *Nicotiana* | *N. benthamiana* | Brassicales | Brassicaceae | *Brassica* | Cauliflower |
| Solanales | Solanaceae | *Nicotiana* | *N. benthamiana* | Brassicales | Brassicaceae | *Brassica* | Cabbage |
| Solanales | Solanaceae | *Petunia* | Petunia | Brassicales | Brassicaceae | *Brassica* | Cabbage |
| Solanales | Solanaceae | *Nicotiana* | *N. benthamiana* | Brassicales | Brassicaceae | *Brassica* | Broccoli |
| Solanales | Solanaceae | *Petunia* | Petunia | Brassicales | Brassicaceae | *Brassica* | Broccoli |
| Solanales | Solanaceae | *Nicotiana* | *N. benthamiana* | Brassicales | Brassicaceae | *Capsella* | *C. rubella* |
| Solanales | Solanaceae | *Nicotiana* | *N. benthamiana* | Brassicales | Brassicaceae | *Cardamine* | *C. hirsuta* |
| Solanales | Solanaceae | *Nicotiana* | *N. tabacum* | Brassicales | Brassicaceae | *Cardamine* | *C. hirsuta* |

TABLE 6

| Scion | | | | Stock | | | |
|---|---|---|---|---|---|---|---|
| Order | Family | Genus | Species | Order | Family | Genus | Species |
| Lamiales | Lamiaceae | *Perilla* | Shiso | Asterales | Asteraceae | *Glebionis* | Crown daisy |
| Lamiales | Lamiaceae | *Perilla* | Shiso | Cucurbitales | Cucurbitaceae | *Cucumis* | Cucumber |
| Lamiales | Lamiaceae | *Perilla* | Shiso | Brassicales | Brassicaceae | *Arabidopsis* | *A. thaliana* (Col) |
| Lamiales | Lamiaceae | *Ocimum* | Basil | Piperales | Saururaceae | *Houttuynia* | *H. cordata* |
| Lamiales | Lamiaceae | *Ocimum* | Basil | Fabales | Fabaceae | *Arachis* | Peanut |
| Lamiales | Lamiaceae | *Lavandula* | Lavender | Solanales | Solanaceae | *Nicotiana* | *N. benthamiana* |

TABLE 7

| Scion | | | | Stock | | | |
|---|---|---|---|---|---|---|---|
| Order | Family | Genus | Species | Order | Family | Genus | Species |
| Cucurbitales | Cucurbitaceae | *Cucumis* | Cucumber | Lamiales | Lamiaceae | *Perilla* | Shiso |
| Gentianales | Apocynaceae | *Vinca* | *V. major* | Lamiales | Lamiaceae | *Perilla* | Shiso |
| Buxales | Buxaceae | *Pachysandra* | *P. terminalis* | Lamiales | Lamiaceae | *Perilla* | Shiso |
| Solanales | Solanaceae | *Nicotiana* | *N. benthamiana* | Lamiales | Lamiaceae | *Perilla* | Shiso |
| Gentianales | Apocynaceae | *Vinca* | *V. major* | Lamiales | Lamiaceae | *Ocimum* | Basil |
| Asterales | Asteraceae | *Chrysanthemum* | Chrysanthemum | Lamiales | Lamiaceae | *Ocimum* | Basil |
| Lamiales | Orobanchaceae | *Phtheirospermum* | *P. japonicum* | Lamiales | Lamiaceae | *Ocimum* | Basil |
| Gentianales | Apocynaceae | *Vinca* | *V. major* | Lamiales | Lamiaceae | *Salvia* | Salvia |
| Solanales | Solanaceae | *Nicotiana* | *N. benthamiana* | Lamiales | Lamiaceae | *Lavandula* | Lavender |

TABLE 8

| Scion | | | | Stock | | | |
|---|---|---|---|---|---|---|---|
| Order | Family | Genus | Species | Order | Family | Genus | Species |
| Lamiales | Orobanchaceae | *Phtheirospermum* | *P. japonicum* | Gentianales | Apocynaceae | *Vinca* | *V. major* |
| Lamiales | Orobanchaceae | *Phtheirospermum* | *P. japonicum* | Asterales | Asteraceae | *Chrysanthemum* | Chrysanthemum |
| Lamiales | Orobanchaceae | *Phtheirospermum* | *P. japonicum* | Fabales | Fabaceae | *Glycine* | Soybean |
| Lamiales | Orobanchaceae | *Phtheirospermum* | *P. japonicum* | Buxales | Buxaceae | *Pachysandra* | *P. terminalis* |
| Lamiales | Orobanchaceae | *Phtheirospermum* | *P. japonicum* | Piperales | Saururaceae | *Houttuynia* | *H. cordata* |
| Lamiales | Orobanchaceae | *Phtheirospermum* | *P. japonicum* | Polypodiales | Dryopteridaceae | *Cyrtomium* | *C. fortunei* |
| Lamiales | Orobanchaceae | *Phtheirospermum* | *P. japonicum* | Fabales | Fabaceae | *Arachis* | Peanut |

TABLE 8-continued

| Scion | | | | Stock | | | |
|---|---|---|---|---|---|---|---|
| Order | Family | Genus | Species | Order | Family | Genus | Species |
| Lamiales | Orobanchaceae | *Phtheirospermum* | *P. japonicum* | Solanales | Solanaceae | *Nicotiana* | *N. benthamiana* |
| Lamiales | Orobanchaceae | *Phtheirospermum* | *P. japonicum* | Brassicales | Brassicaceae | *Arabidopsis* | *A. thaliana* (Col) |

TABLE 9

| Scion | | | | Stock | | | |
|---|---|---|---|---|---|---|---|
| Order | Family | Genus | Species | Order | Family | Genus | Species |
| Gentianales | Apocynaceae | *Vinca* | *V. major* | Lamiales | Orobanchaceae | *Phtheirospermum* | *P. japonicum* |
| Asterales | Asteraceae | *Chrysanthemum* | *Chrysanthemum* | Lamiales | Orobanchaceae | *Phtheirospermum* | *P. japonicum* |
| Cucurbitales | Cucurbitaceae | *Cucumis* | Cucumber | Lamiales | Orobanchaceae | *Phtheirospermum* | *P. japonicum* |
| Solanales | Solanaceae | *Nicotiana* | *N. benthamiana* | Lamiales | Orobanchaceae | *Phtheirospermum* | *P. japonicum* |

As shown in these tables and FIG. 3, plants belonging to the Solanaceae, Brassicaceae, Lamiaceae, and Orobanchaceae could serve as stocks and/or scions to allow grafting with various plants.

Example 2

Production of Two-Species Grafted Plant Body Using Interstock

Grafting by the interstock method comprises a stock, an interstock, and a scion. Therefore, grafting was performed between a stock and an interstock, and between an interstock and a scion. When grafting was performed in two places at the same time, first, the stem (including about two knots) of a plant used as an interstock was cut, and a scion was assembled at the tip of the stem in the originally growing direction. Subsequently, the end of the stem of the interstock/scion on the interstock side was assembled to the stem of a stock. When grafting was performed in two places on different days in two steps, first, grafting was performed between a plant as a stock and a plant as an interstock. Then, the state of graft was confirmed to be good at the first or second week after grafting, and a scion was grafted on the plant as an interstock.

Alternatively, grafting was performed independently between a plant as a stock and a plant as an interstock, and between a plant as an interstock and a plant as a scion. As for those for which the state of graft was confirmed to be good at the first or second week after grafting, grafting was newly applied to the stem of each plant as the interstock. Thus, a stock/interstock/interstock/scion was obtained. Tables 10 and 11 show examples of successful grafting.

TABLE 10

| Scion | | | | | Stock | | | |
|---|---|---|---|---|---|---|---|---|
| Order | Family | Genus | Species | Interstock | Order | Family | Genus | Species |
| Gentianales | Apocynaceae | *Catharanthus* | *C. roseus* | Nb | Fabales | Fabaceae | *Vicia* | Broad bean |
| Gentianales | Apocynaceae | *Vinca* | *V. major*/Nb | Nb | Asterales | Asteraceae | *Chrysanthemum* | *Chrysanthemum* |
| Asterales | Asteraceae | *Chrysanthemum* | *Chrysanthemum* | Nb | Gentianales | Apocynaceae | *Vinca* | *V. major* |
| Asterales | Asteraceae | *Glebionis* | Crown daisy | Nb | Gentianales | Apocynaceae | *Catharanthus* | *C. roseus* |
| Gentianales | Apocynaceae | *Catharanthus* | *C. roseus* | Nb | Brassicales | Brassicaceae | *Arabidopsis* | *A. thaliana* (Col) |
| Gentianales | Apocynaceae | *Vinca* | *V. major*/Nb | Nb | Brassicales | Brassicaceae | *Arabidopsis* | *A. thaliana* (Col) |
| Asterales | Asteraceae | *Chrysanthemum* | *Chrysanthemum* | Nb | Brassicales | Brassicaceae | *Arabidopsis* | *A. thaliana* (Col) |
| Asterales | Asteraceae | *Chrysanthemum* | *Chrysanthemum* | Nb | Brassicales | Brassicaceae | *Brassica* | Broccoli |
| Asterales | Asteraceae | *Glebionis* | Crown daisy | Nb | Brassicales | Brassicaceae | *Arabidopsis* | *A. thaliana* (Col) |
| Solanales | Solanaceae | *Solanum* | Micro-Tom | Nb | Fabales | Fabaceae | *Vicia* | Broad bean |
| Solanales | Solanaceae | *Solanum* | Micro-Tom | Nb | Asterales | Asteraceae | *Chrysanthemum* | *Chrysanthemum* |
| Solanales | Solanaceae | *Solanum* | Micro-Tom | *Petunia* | Asterales | Asteraceae | *Chrysanthemum* | *Chrysanthemum* |
| Solanales | Solanaceae | *Petunia* | *Petunia* | Nb | Brassicales | Brassicaceae | *Brassica* | Cauliflower |
| Solanales | Solanaceae | *Petunia* | *Petunia* | Nb | Brassicales | Brassicaceae | *Brassica* | Broccoli |
| Solanales | Solanaceae | *Solanum* | Micro-Tom | Nb | Brassicales | Brassicaceae | *Arabidopsis* | *A. thaliana* (Col) |
| Solanales | Solanaceae | *Solanum* | Ponderosa tomato | Nb | Brassicales | Brassicaceae | *Arabidopsis* | *A. thaliana* (Col) |

TABLE 11

| Scion | | | | | Stock | | | |
|---|---|---|---|---|---|---|---|---|
| Order | Family | Genus | Species | Interstock | Order | Family | Genus | Species |
| Gentianales | Apocynaceae | *Catharanthus* | *C. roseus* | *P. japonicum* | Cucurbitales | Cucurbitaceae | *Cucumis* | Cucumber |

As shown in the tables, it was revealed that the plants belonging to the genus *Nicotiana* of the Solanaceae family, such as *Nicotiana benthamiana*, allowed grafting between plant tissues of plants that were considered to have poor graft compatibility, such as plants belonging to different families, through their own plant tissue. The above results demonstrated that when a certain species of plant tissue was graft-compatible with two or more plants by grafting with a scion/stock structure, the use of this plant tissue as an interstock allowed grafting between plant tissues of plants that originally had poor graft compatibility.

Example 3

Confirmation of Apoplastic Transport

Figure 4:
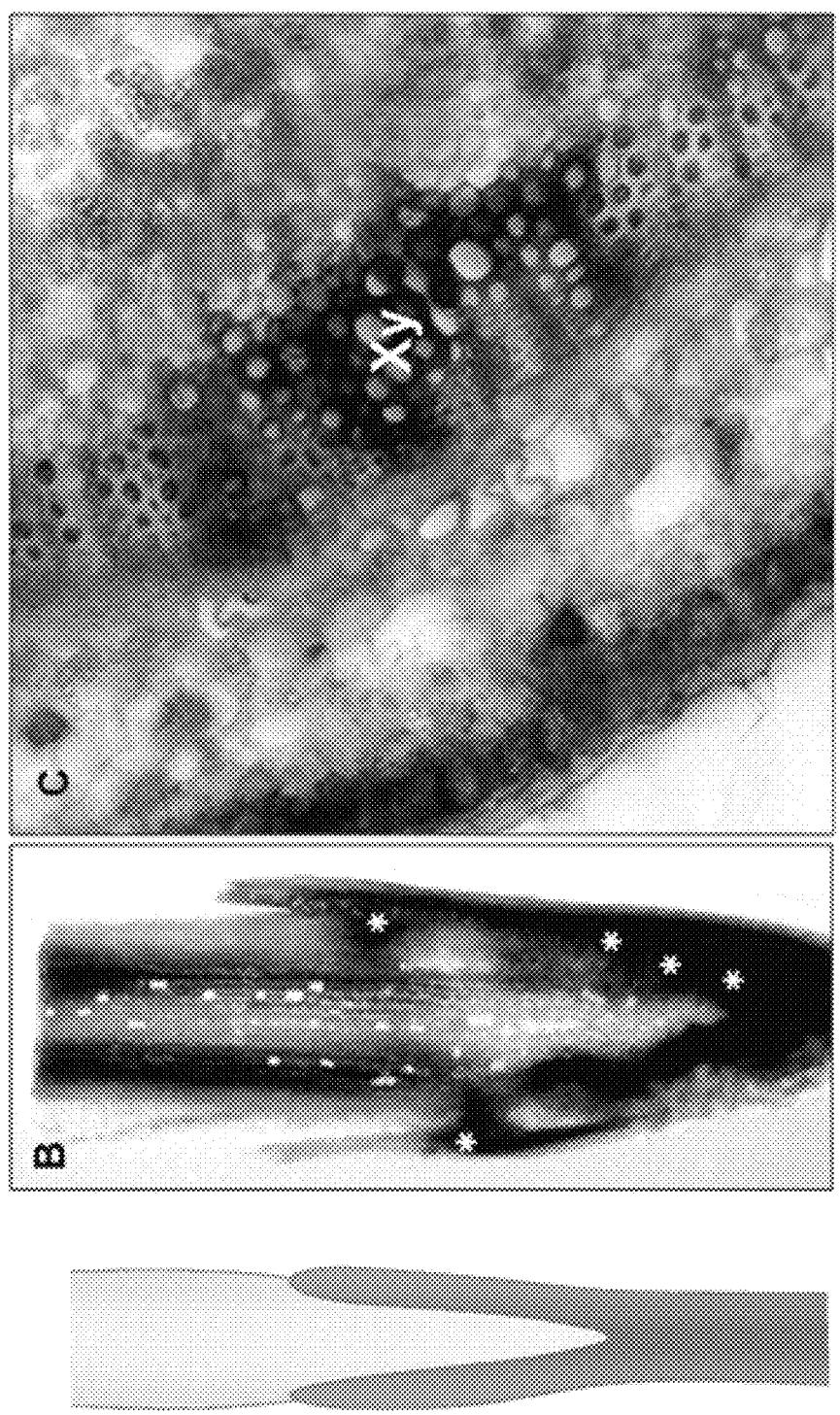
FIG. 4 shows confirmation results of apoplastic transport.

The tests of Examples 3 to 9 were conducted on grafting between a *Nicotiana benthamiana* scion and an *Arabidopsis thaliana* stock at the third week after grafting. A flower stalk of the stock was horizontally cut near the root to cut off the scion together with the flower stalk of the stock. 2 or 3 longitudinal incisions were made on the cut surface on the stock side, and the cut stem was placed in a 0.5% toluidine blue aqueous solution dispensed in a 1.5-mL tube to allow the stem to absorb the solution. 3 to 6 hours later, longitudinal or traverse free-hand sections of the graft connection, and the stem (a region close to the graft site) of the scion were produced. Then, it was confirmed and photographed using a stereoscopic microscope or an optical microscope that the blue color of the toluidine blue reagent was observed in vessel elements on the scion side. FIG. 4 shows the results. Of FIG. 4, A shows a schematic diagram of grafting, and B and C show the observation results of the longitudinal and transverse cross-sections of the stock absorbing toluidine blue.

As shown in FIG. 3, it was revealed that the ink was transported from the stock to the scion. It was also revealed that the ink was transported through the vessels.

Example 4

Figure 5:
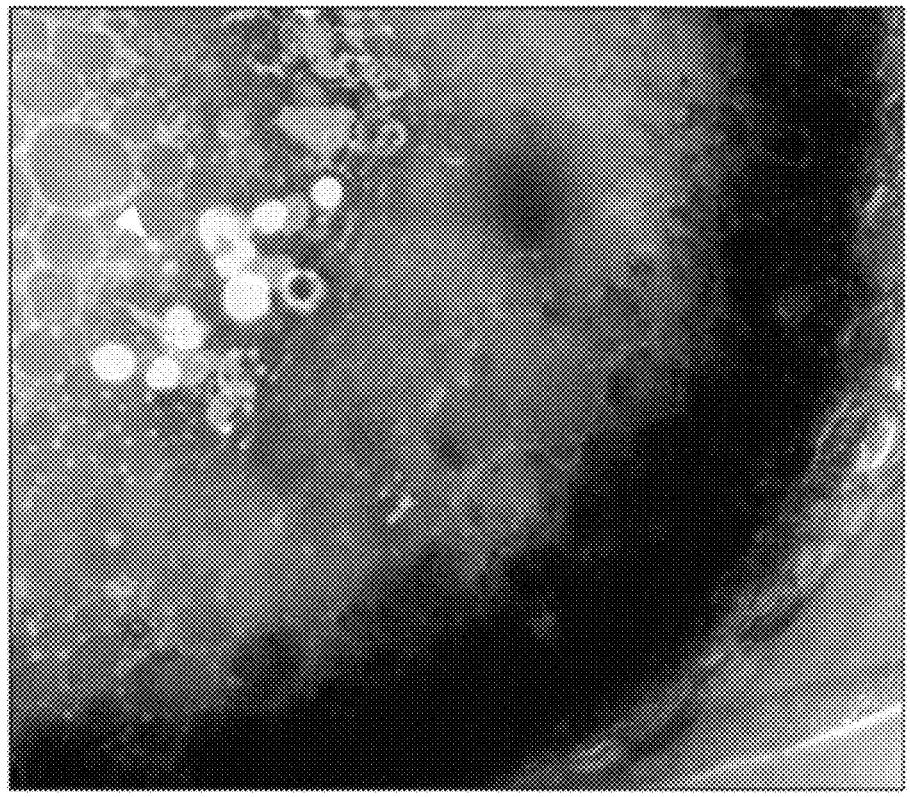
FIG. 5 shows confirmation results of symplastic transport.
Figure 5:
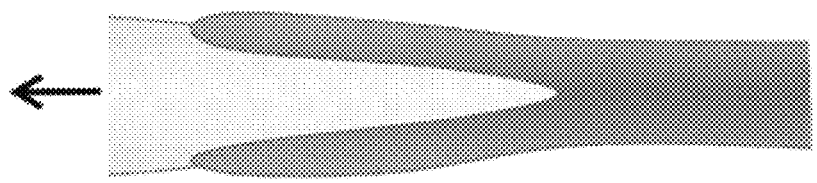

Confirmation 1 of Symplastic Transport 0.5 mg/mL of 5(6)-carboxyfluorescein diacetate (CFDA), which was a tracer for symplastic transport, was administered to 5 to 10 mature leaves (rosette leaves) of the stock, and one cauline leaf located below the graft site. A stock solution of CFDA adjusted with acetone to 50 mg/mL and stored at −20° C. was used in the experiment. When the localization pattern of carboxyfluorescein was examined, propidium iodide (PI) transported by apoplastic transport was also administered simultaneously with CFDA so as to easily differentiate the localization pattern from the pattern of apoplastic transport through the vessels. PI was added to the CFDA solution so that the final concentration was 1 mg/mL. A plurality of PCR tubes with their tip cut off was prepared as vessels, and about 50 µL of the CFDA solution was applied to each tube. 3 to 5 longitudinal incisions of about 5 mm were made at the tip of the leaves, and the leaves were placed in each of the prepared vessels containing the CFDA solution so that the incisions were exposed to the solution. The entire grafted seedling was covered with a plastic bag to prevent the vaporization of a small amount of the CFDA solution. Administration was continued overnight. On the next day, a traverse free-hand section of the apical region (1 to 2 cm from the growing point) of the scion was produced, and observed and photographed by a confocal microscope. FIG. 5 shows the results. A shows a schematic diagram of the graft site, and B shows the observation results of the transverse section (apical region distal from the graft site) of the scion.

As shown in FIG. 5, the tracer administered to the mature leaf of the stock was detected as dye from the sieve tubes of the scion. These results demonstrated that symplastic transport occurred through the graft site.

Example 5

Confirmation 2 of Symplastic Transport

Figure 6:
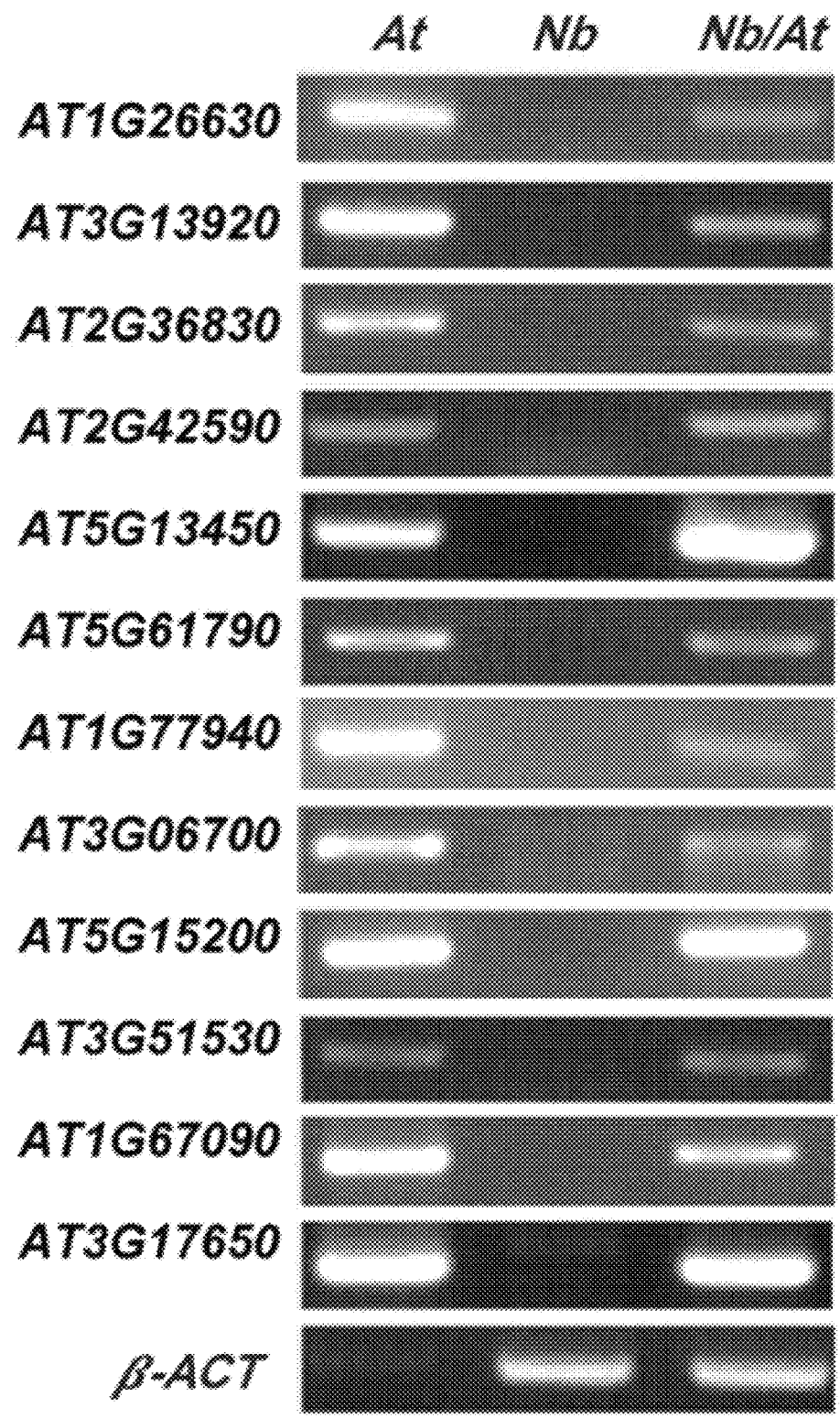
FIG. 6 shows other confirmation results of symplastic transport.

The movement of mRNA was detected by the RT-PCR assay. A primer specific to *Arabidopsis thaliana* was prepared to differentiate *Arabidopsis thaliana* from *Nicotiana benthamiana*. The analysis was performed using ungrafted *Arabidopsis thaliana* as a positive control, ungrafted *Nicotiana benthamiana* as a negative control, and a *Nicotiana benthamiana* scion grafted with an *Arabidopsis thaliana* stock as a starting sample. Total RNA was extracted from each sample using a TRIzol reagent (Life Technologies). cDNA was synthesized using SuperScript III (Life Technologies), and used as a template for RT-PCR. PCR reactions were carried out for 40 cycles. When amplification was not confirmed thereby, the second PCR was further carried out for 30 cycles using part of the first PCR product as a template. PCR products were electrophoresed using agarose gel, the gel was stained with ethidium bromide, and the band pattern was confirmed. As for the band amplified from the sample of the *Nicotiana benthamiana* scion, the gel was cut and purified, and cloned into a plasmid vector. It was confirmed, by a sequence reaction, that the sequence of *Arabidopsis thaliana* was amplified. FIG. 6 shows the results. In this figure, At (*Arabidopsis thaliana*) represents the ungrafted *Arabidopsis thaliana*, Nb represents the ungrafted *Nicotiana benthamiana*, and Nb/At represents the *Nicotiana benthamiana* scion grafted with the *Arabidopsis thaliana* stock.

As shown in FIG. 6, migrating mRNA derived from At was detected from the scion of the Nb/At graft. These results demonstrated that mRNA was symplastically transported from the stock to the scion across the graft site.

Example 6

Confirmation 3 of Symplastic Transport

Figure 7:
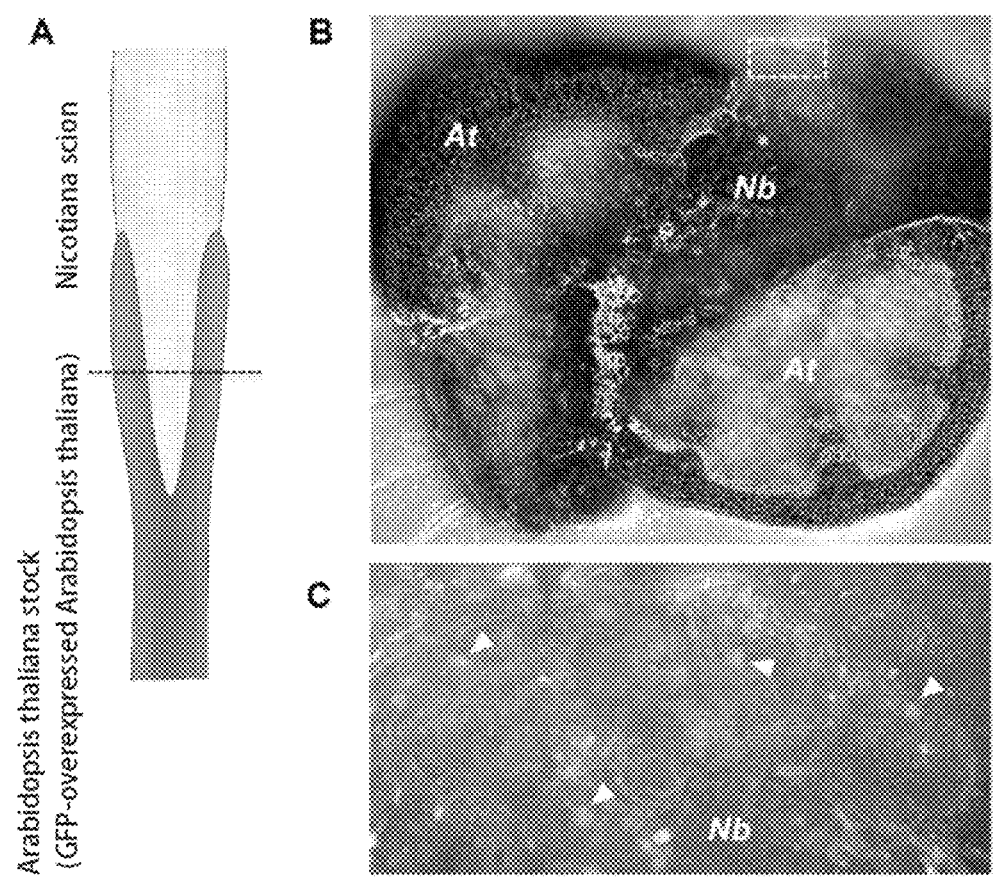
FIG. 7 shows other confirmation results of symplastic transport.

The movement of GFP protein was detected in the following manner. *Nicotiana benthamiana* as a scion was grafted with GFP-overexpressed *Arabidopsis thaliana* (35S: GFP) as a stock, and a traverse free-hand section of the graft connection was produced, and observed and photographed by a confocal microscope. FIG. 7 shows the results. A shows a schematic diagram of the graft site, B shows the observation results of the transverse section of the graft site, and C shows the magnified observation results of the dotted-line area in B.

As shown in FIG. 7, it was revealed that GFP was symplastically transported from the stock to the scion across the graft site.

Example 7

Histological Observation of Vessel Element

Figure 8:
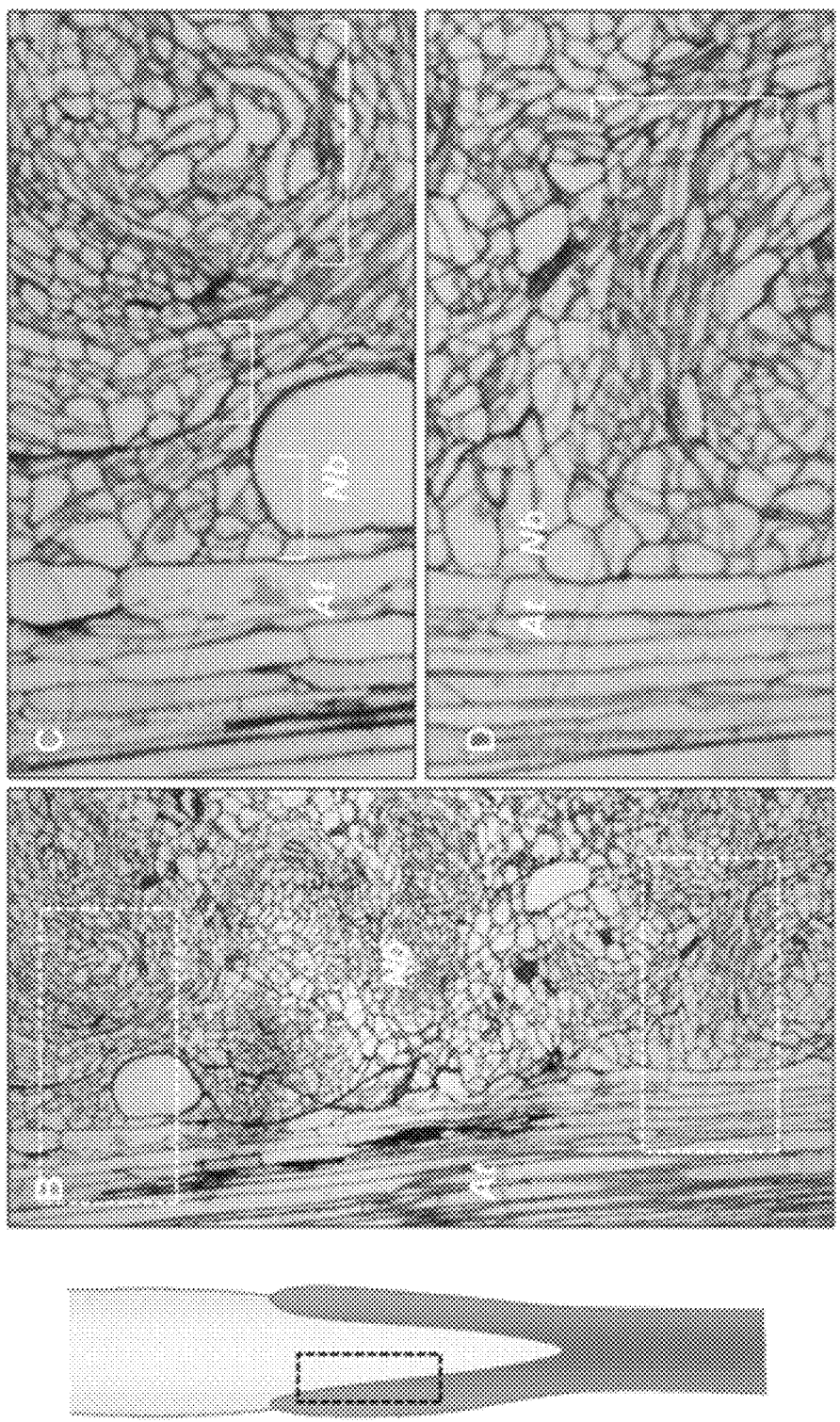
FIG. 8 shows histological observation results of vessel elements.

The graft site was cut, and a traverse free-hand section with a thickness of several hundreds of µm was produced under a stereoscopic microscope while immersing the sample in a fixing solution (2% paraformaldehyde, 2% glutaraldehyde, 0.05 M cacodylate buffer, pH 7.4). After degassing was repeated several times in a fixing solution with the same composition, fixation was performed at 4° C. overnight. On the next day, washing with a 0.05 M cacodylate buffer was performed 3 times for 30 minutes per time. Then, fixation was performed in another fixing solution (2% osmium tetroxide, 0.05 M cacodylate buffer, pH 7.4) at 4° C. for 3 hours. The sample was dehydrated with ethanol, and then embedded in Quetol-651 resin (Nisshin EM). A section with a thickness of 150 µm was produced by a microtome, stained with a 0.5% toluidine blue aqueous solution, and observed and photographed by an optical microscope. FIG. 8 shows the results. A shows a schematic diagram of the graft site, and the dotted line shows the observed area. B shows the observation results of the longitudinal section of the graft site, and C and D show the magnified observation results of the dotted-line areas in B.

As shown in FIG. 8, it was revealed that vessel elements were formed in random directions in the parenchyma developed in the scion.

Example 8

Histological Observation of Sieve Tube Element

Figure 9:
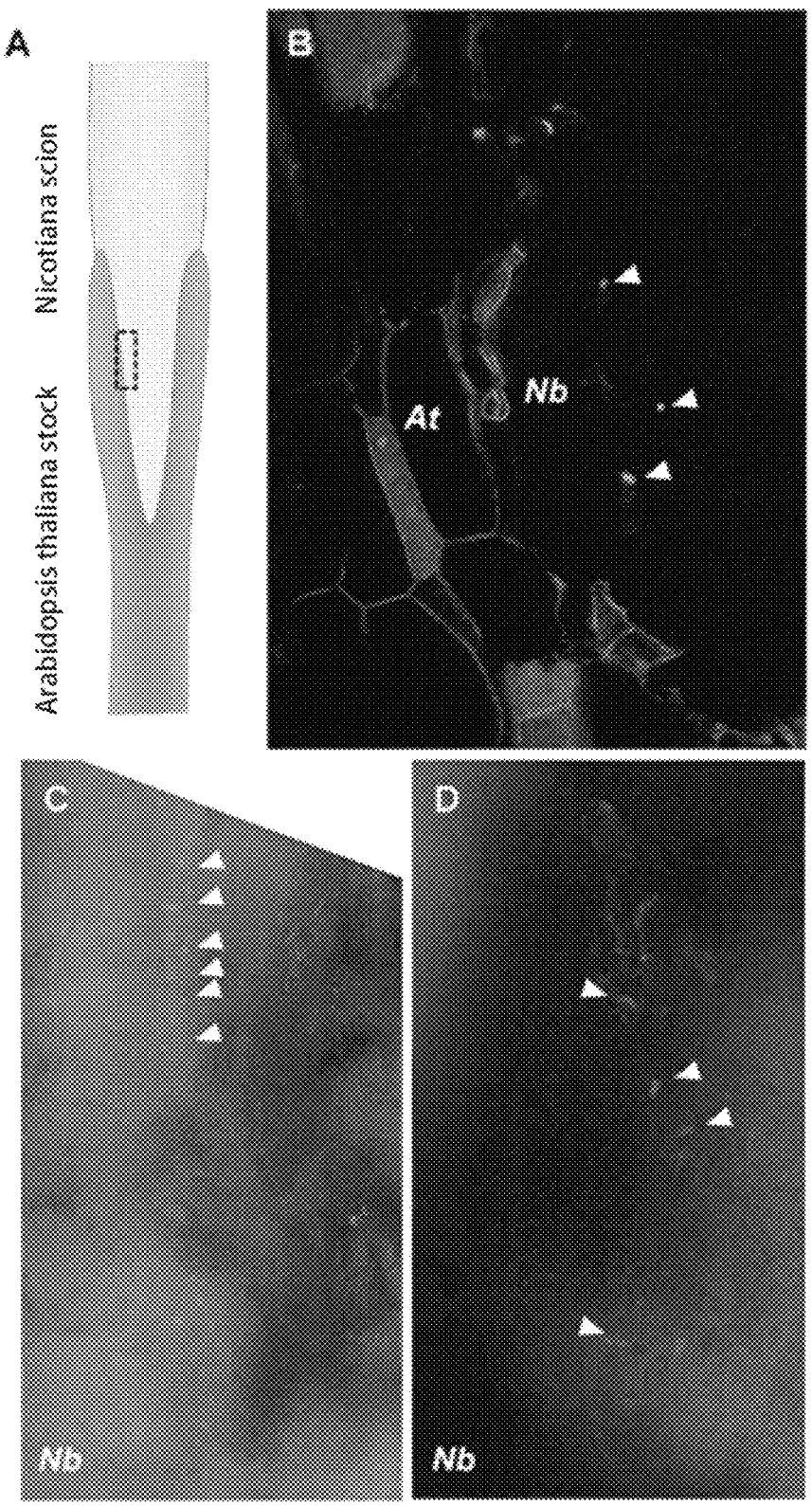
FIG. 9 shows histological observation results of sieve tube elements.

Nicotiana benthamiana as a scion was grafted with Arabidopsis thaliana cell membrane-localized tdTomato-expressed body (RPS5 A: tdTomato-LTI6b) as a stock, and a longitudinal free-hand section of the graft connection was produced. The section was stained with a 0.1% aniline blue aqueous solution, and observed and photographed by a confocal microscope. FIG. 9 shows the results. A shows a schematic diagram of the graft site, and the dotted line shows the observed area. B shows a longitudinal cross-sectional image of the graft site, and C and D show other longitudinal cross-sectional images.

As shown in FIG. 9, due to the aniline-blue staining of callose accumulated in the cribriform plate, the end of individual cells constituting sieve tubes was stained depending on the presence of sieve tubes, and continuous luminescent spots were observed. These results revealed that sieve tube elements were formed in random directions in the parenchyma developed in the scion.

Example 9

Cytomorphologic Observation of de novo Formation of Plasmodesmata

Figure 10:
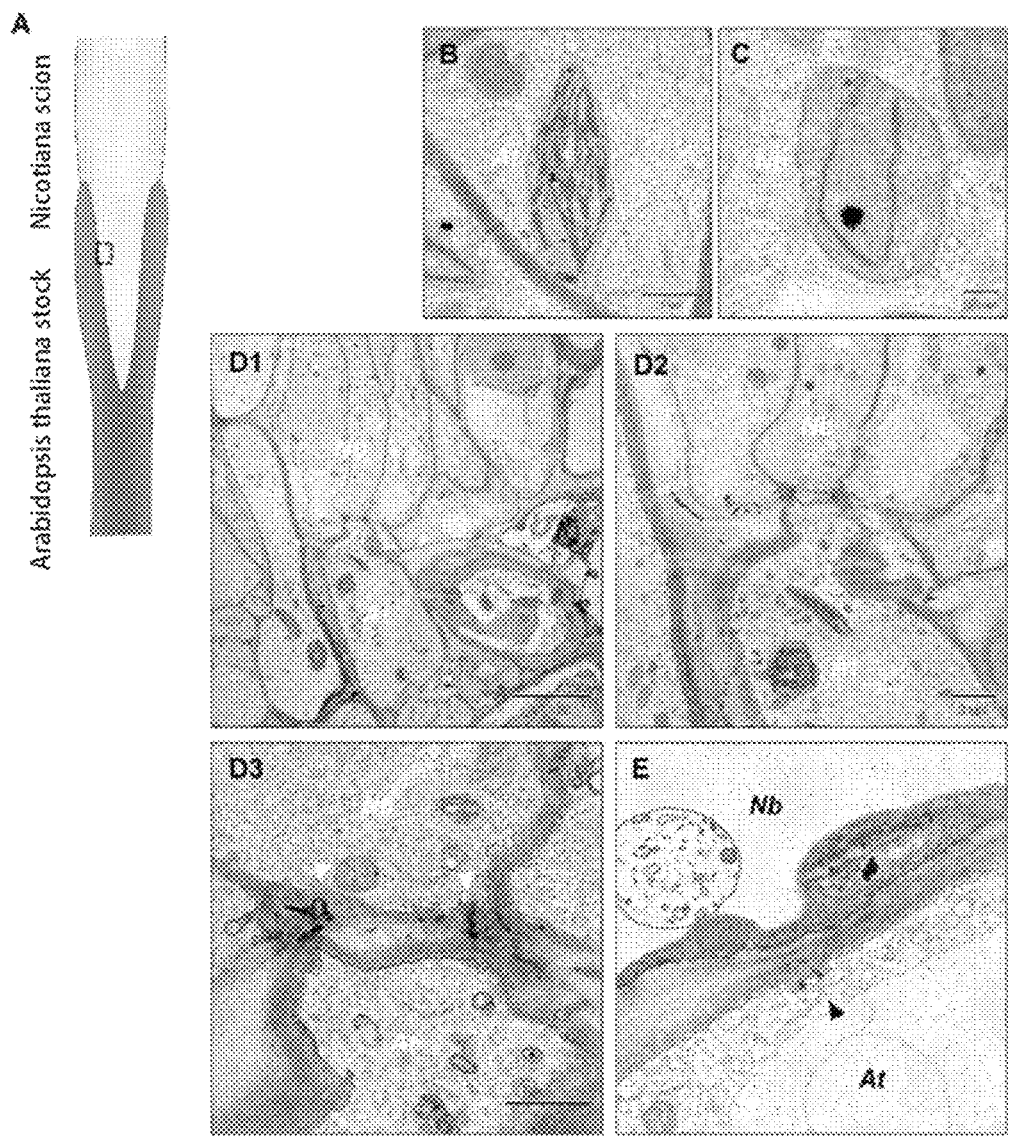
FIG. 10 shows cytomorphologic observation results of de novo formation of plasmodesmata.

A resin block of the sample was prepared in the same manner as in the histological observation of the vessel elements. A section with a thickness of 120 nm was produced by an ultramicrotome, and the resulting section was mounted on a copper grid. The mounted section was stained with a 2% uranyl acetate solution at room temperature for 15 minutes. After washing with distilled water, secondary staining was performed using a lead stain solution (Sigma-Aldrich) at room temperature for 3 minutes. The sample was observed and photographed by an electron microscope. The graft boundary region was identified using, as indexes, plastids having a form characteristic to each of Arabidopsis thaliana and Nicotiana. FIG. 10 shows the results. A shows a schematic diagram of the graft site, and the dotted line shows the observed area. B shows Arabidopsis thaliana plastid, C shows Nicotiana plastid, D shows enlarged images of the boundary region between Arabidopsis thaliana and Nicotiana, and E shows an enlarged image of another boundary region between Arabidopsis thaliana and Nicotiana.

As shown in FIG. 10, it was revealed that plasmodesmata between Arabidopsis thaliana and Nicotiana were newly formed in the graft site.

The above results demonstrated that in plants belonging to the family Solanaceae (Nicotiana), or plants belonging to the family Brassicaceae (Arabidopsis), parenchyma was developed and fused in the graft site; sieve tube elements and vessel elements were developed in the parenchyma, although their orientation was distorted; and plasmodesmata were newly formed at the cellular level. As a result, apoplastic and symplastic transport was achieved, and a graft site in a form that did not conventionally exist was formed. It was considered that, due to transport and communication through the mutual parenchyma, the completion of grafting between plants that generally had poor graft compatibility (e.g., different-family plants) was promoted.

Example 10

Figure 11:
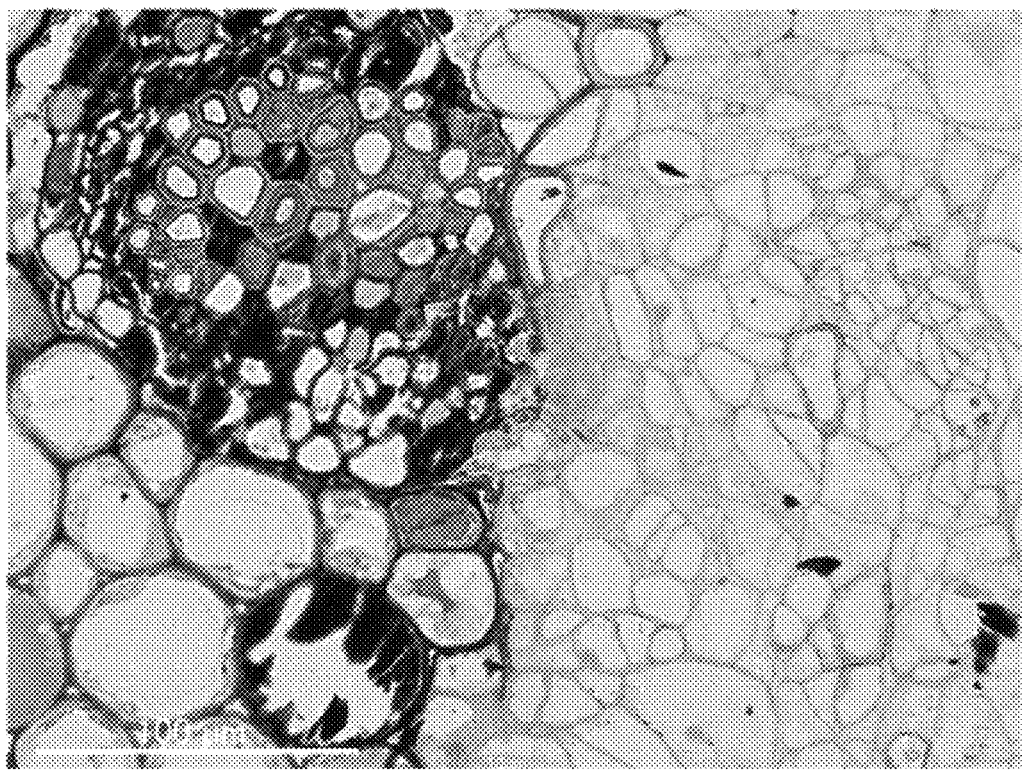
FIG. 11 shows tissue fusion between a *Nicotiana* plant and a fern.

The tests of Examples 10 and 11 were performed on grafting between a Nicotiana benthamiana scion and a fern (Cyrtomium fortunei) stock at the first month after grafting. The graft site was cut, and a traverse free-hand section with a thickness of several hundreds of µm was produced under a stereoscopic microscope while immersing the sample in a fixing solution (2% paraformaldehyde, 2% glutaraldehyde, 0.05 M cacodylate buffer, pH 7.4). After degassing was repeated several times in a fixing solution with the same composition, fixation was performed at 4° C. overnight. On the next day, washing with a 0.05 M cacodylate buffer was performed 3 times for 30 minutes per time. Then, fixation was performed in another fixing solution (2% osmium tetroxide, 0.05 M cacodylate buffer, pH 7.4) at 4° C. for 3 hours. The sample was dehydrated with ethanol, and then embedded in Quetol-651 resin (Nisshin EM). A section with a thickness of 150 µm was produced by a microtome, stained with a 0.5% toluidine blue aqueous solution, and observed and photographed by an optical microscope. FIG. 11 shows the results.

As shown in FIG. 11, it was observed that the tissue of the Nicotiana plant was fused with the vascular bundle of the fern.

Example 11

Figure 12:
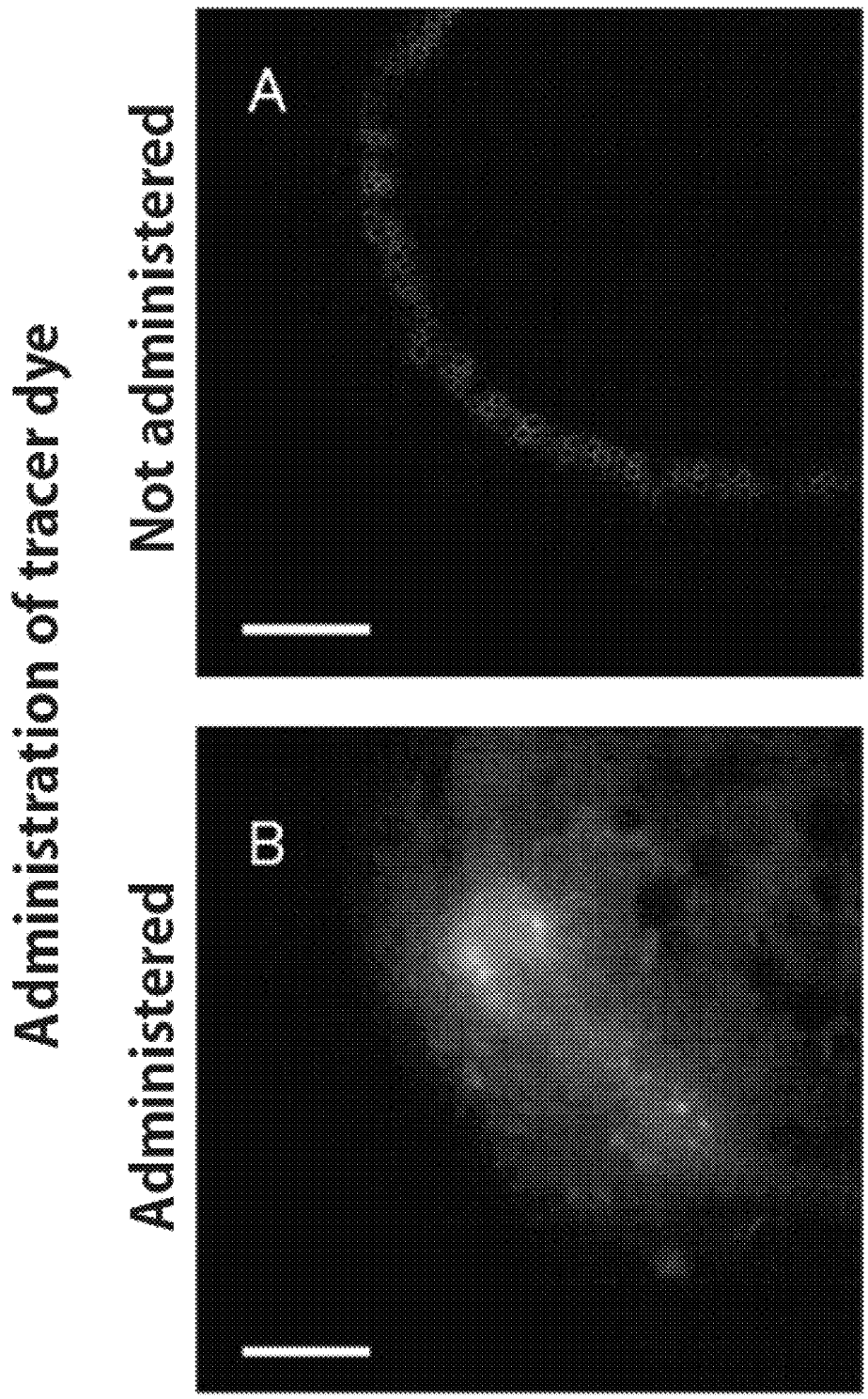
FIG. 12 shows confirmation results of symplastic transport between a *Nicotiana* plant and a fern.

A fern (Cyrtomium fortunei) stock was cut, and 0.1 mg/mL of 5(6)-carboxyfluorescein diacetate (CFDA), which was a tracer for symplastic transport, was administered to the cut petiole. As a comparison, the stem of an N. benthamiana scion grafted with an untreated fern (Cyrtomium fortunei) stock was examined. A stock solution of CFDA adjusted with acetone to 50 mg/mL and stored at −20° C. was used in the experiment. 2 or 3 longitudinal incisions of about 5 mm were made at the tip of the cut petiole, and the petiole was placed in a prepared 1.5-ml tube containing the CFDA solution so that the incisions were exposed to the solution. The opening of the 1.5-mL tube containing the solution was covered with parafilm to prevent the vaporization of a small amount of the CFDA solution. Administration was continued for 8 hours. A traverse free-hand section of the apical region of the scion was produced, and observed and photographed with a fluorescence microscope. FIG. 12 shows the results. FIG. 12A shows a transverse section of the scion without CFDA administration to the stock, and FIG. 12B shows the observation results of a transverse section of the scion with CFDA administration to the stock.

As shown in FIG. 12, the tracer injected into the fern as the stock was detected in the *Nicotiana* plant as the scion. This revealed that symplastic transport occurred between the fern and the *Nicotiana* plant through the graft site.

The above results indicated that tissue fusion and symplastic transport occurred between plants belonging to the Solanaceae (*Nicotiana*) and ferns, which are evolutionarily far from the Solanaceae (*Nicotiana*) plants, thereby leading to the completion of grafting. This suggested that any plants evolutionarily closer than ferns can be grafted with plants belonging to the Solanaceae (*Nicotiana*).

The invention claimed is:

1. A plant tissue comprising two different-family plant tissues grafted through a graft medium, the graft medium including a plant tissue of *Nicotiana benthamiana* in which the graft medium has two surfaces cut for grafting and is an interstock between the two different-family plants,
wherein each of the two different-family plant tissues belongs to a genus selected from the group consisting of *Capsella, Cardamine, Abelia, Alternanthera, Anemone, Anthurium, Antirrhinum, Arachis, Buckleya, Callistephus, Cardiospermum, Catharanthus, Chamaecyparis, Chrysanthemum, Cinnamomum, Citrus, Cleome, Consolida, Cryptotaenia, Cucumis, Cyrtomium, Daucus, Eustoma, Fallopia, Fragaria, Gentiana, Geranium, Glycine, Gossypium, Grevillea, Heucherella, Houttuynia, Ipomoea, Lavandula, Lotus, Malus, Medicago, Melilotus, Pachira, Pachysandra, Perilla, Phtheirospermum, Pisum, Populus, Quercus, Rhododendron, Rosa, Salix, Sarcandra, Scabiosa, Sesamum, Spinacia, Stevia, Trifolium, Trigonella, Vaccinium, Vicia, Vigna, Vinca, Viola*, and *Vitis*.

2. A method for producing a plant tissue, comprising grafting two different-family plant tissues through a graft medium, the graft medium including a plant tissue of *Nicotiana benthamiana*, wherein the graft medium has two surfaces cut for grafting and is an interstock between the two different-family plant tissues belongs to a genus selected from the group consisting of *Capsella Cardamine, Abelia, Alternanthera, Anemone, Anthurium, Antirrhinum, Arachis, Buckleya, Callistephus, Cardiospermum, Catharanthus, Chamaecyparis, Chrysanthemum, Cinnamomum, Citrus, Cleome, Consolida, Cryptotaenia, Cucumis, Cyrtomium, Daucus, Eustoma, Fallopia, Fragaria, Gentiana, Geranium, Glycine, Gossypium, Grevillea, Heucherella, Houttuynia, Ipomoea, Lavandula, Lotus, Malus, Medicago, Melilotus, Pachira, Pachysandra, Perilla, Phtheirospermum, Pisum, Populus, Quercus, Rhododendron, Rosa, Salix, Sarcandra, Scabiosa, Sesamum, Spinacia, Stevia, Trifolium, Trigonella, Vaccinium, Vicia, Vigna, Vinca, Viola*, and *Vitis*.

3. A plant tissue comprising a first plant tissue of *Nicotiana benthamiana* and a different-family plant tissue grafted with the first plant tissue, in which the first plant tissue has a surface cut for grafting,
wherein the different-family plant tissue belongs to a genus selected from the group consisting of *Capsella, Cardamine, Abelia, Alternanthera, Anemone, Anthurium, Antirrhinum, Arachis, Buckleya, Callistephus, Cardiospermum, Catharanthus, Chamaecyparis, Chrysanthemum, Cinnamomum, Citrus, Cleome, Consolida, Cryptotaenia, Cucumis, Cyrtomium, Daucus, Eustoma, Fallopia, Fragaria, Gentiana, Geranium, Glycine, Gossypium, Grevillea, Heucherella, Houttuynia, Ipomoea, Lavandula, Lotus, Malus, Medicago, Melilotus, Pachira, Pachysandra, Perilla, Phtheirospermum, Pisum, Populus, Quercus, Rhododendron, Rosa, Salix, Sarcandra, Scabiosa, Sesamum, Spinacia, Stevia, Trifolium, Trigonella, Vaccinium, Vicia, Vigna, Vinca, Viola*, and *Vitis*.

4. A plant body comprising the plant tissue according to claim 1.

5. The plant body according to claim 4, further comprising a plant tissue of a cultivar.

6. A method for producing a crop, comprising harvesting a crop from the plant body according to claim 5.

7. A method for identifying a graft medium between two different-family plants, comprising steps (a) to (c):
(a) grafting a subject plant tissue with a different-family plant tissue to obtain a plant body, in which the subject plant tissue is a plant tissue of *Nicotiana benthamiana*, wherein the different-family plant tissue belongs to a genus selected from the group consisting of *Capsella, Cardamine, Abelia, Alternanthera, Anemone, Anthurium, Antirrhinum, Arachis, Buckleya, Callistephus, Cardiospermum, Catharanthus, Chamaecyparis, Chrysanthemum, Cinnamomum, Citrus, Cleome, Consolida, Cryptotaenia, Cucumis, Cyrtomium, Daucus, Eustoma, Fallopia, Fragaria, Gentiana, Geranium, Glycine, Gossypium, Grevillea, Heucherella, Houttuynia, Ipomoea, Lavandula, Lotus, Malus, Medicago, Melilotus, Pachira, Pachysandra, Perilla, Phtheirospermum, Pisum, Populus, Quercus, Rhododendron, Rosa, Salix, Sarcandra, Scabiosa, Sesamum, Spinacia, Stevia, Trifolium, Trigonella, Vaccinium, Vicia, Vigna, Vinca, Viola*, and *Vitis*;
(b) culturing the plant body; and
(c) when the cultured plant body does not die, selecting the subject plant tissue as a graft medium between two different-family plants.

8. A method for identifying a graft medium between two different-family plants, comprising steps (d) to (f):
(d) grafting two plant tissues of two different-family plants through a subject plant tissue to obtain a plant body, wherein the subject plant tissue is a plant tissue of *Nicotiana benthamiana* and is an interstock between the two different-family plants, wherein each of the two different-family plant tissues belongs to a genus selected from the group consisting of *Abelia, Alternanthera, Anemone, Anthurium, Antirrhinum, Arachis, Buckleya, Callistephus, Capsella, Cardamine, Cardiospermum, Catharanthus, Chamaecyparis, Chrysanthemum, Cinnamomum, Citrus, Cleome, Consolida, Cryptotaenia, Cucumis, Cyrtomium, Daucus, Eustoma, Fallopia, Fragaria, Gentiana, Geranium, Glycine, Gossypium, Grevillea, Heucherella, Houttuynia, Ipomoea, Lavandula, Lotus, Malus, Medicago, Melilotus, Pachira, Pachysandra, Perilla, Phtheirospermum, Pisum, Populus, Quercus, Rhododendron, Rosa, Salix, Sarcandra, Scabiosa, Sesamum, Spinacia, Stevia, Trifolium, Trigonella, Vaccinium, Vicia, Vigna, Vinca, Viola*, and *Vitis*;
(e) culturing the plant body; and
(f) when the cultured plant body does not die, selecting the subject plant tissue as a graft medium between two different-family plants.

9. A delivery medium for delivering a useful component to a different-family plant, the delivery medium comprising a plant tissue of *Nicotiana benthamiana* and having a surface cut for grafting,
wherein the different-family plant tissue belongs to a genus selected from the group consisting of *Capsella, Cardamine, Abelia, Alternanthera, Anemone, Anthurium, Antirrhinum, Arachis, Buckleya, Callistephus, Cardiospermum, Catharanthus, Chamaecyparis, Chrysanthemum, Cinnamomum, Citrus, Cleome, Consolida, Cryptotaenia, Cucumis, Cyrtomium, Daucus, Eustoma, Fallopia, Fragaria, Gentiana, Geranium, Glycine, Gossypium, Grevillea, Heucherella, Houttuynia, Ipomoea, Lavandula, Lotus, Malus, Medicago,*

*Melilotus, Pachira, Pachysandra, Perilla, Phtheirospermum, Pisum, Populus, Quercus, Rhododendron, Rosa, Salix, Sarcandra, Scabiosa, Sesamum, Spinacia, Stevia, Trifolium, Trigonella, Vaccinium, Vicia, Vigna, Vinca, Viola,* and *Vitis.*

10. A plant tissue comprising the delivery medium according to claim 9 grafted with a different-family plant tissue.

11. A plant body comprising the plant tissue according to claim 10.

12. A method for producing a plant body to which a useful component is delivered, the method comprising delivering a useful component to a plant body through a delivery medium, in which the delivery medium is grafted with a different-family plant tissue, the plant body contains the delivery medium, and the delivery medium comprises a plant tissue of *Nicotiana benthamiana* and has a surface cut for grafting, wherein the different-family plant tissue belongs to a genus selected from the group consisting of *Capsella, Cardamine, Abelia, Alternanthera, Anemone, Anthurium, Antirrhinum, Arachis, Buckleya, Callistephus, Cardiospermum, Catharanthus, Chamaecyparis, Chrysanthemum, Cinnamomum, Citrus, Cleome, Consolida, Cryptotaenia, Cucumis, Cyrtomium, Daucus, Eustoma, Fallopia, Fragaria, Gentiana, Geranium, Glycine, Gossypium, Grevillea, Heucherella, Houttuynia, Ipomoea, Lavandula, Lotus, Malus, Medicago, Melilotus, Pachira, Pachysandra, Perilla, Phtheirospermum, Pisum, Populus, Quercus, Rhododendron, Rosa, Salix, Sarcandra, Scabiosa, Sesamum, Spinacia, Stevia, Trifolium, Trigonella, Vaccinium, Vicia, Vigna, Vinca, Viola,* and *Vitis.*

13. A plant body comprising the plant tissue according to claim 3.

14. The plant body according to claim 13, further comprising a plant tissue of a cultivar.

15. A method for producing a crop, comprising harvesting a crop from the plant body according to claim 14.

* * * * *